(12) United States Patent
Bennett et al.

(10) Patent No.: US 7,678,895 B2
(45) Date of Patent: *Mar. 16, 2010

(54) ANTISENSE MODULATION OF SUPEROXIDE DISMUTASE 1, SOLUBLE EXPRESSION

(75) Inventors: C. Frank Bennett, Carlsbad, CA (US); Susan M. Freier, San Diego, CA (US); Thomas P. Condon, Singapore (SG)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 11/449,207

(22) Filed: Jun. 7, 2006

(65) Prior Publication Data

US 2006/0293269 A1 Dec. 28, 2006

Related U.S. Application Data

(63) Continuation of application No. 10/672,866, filed on Sep. 26, 2003, now abandoned, which is a continuation-in-part of application No. 10/633,843, filed on Aug. 4, 2003, now Pat. No. 7,132,530, which is a continuation of application No. 09/888,360, filed on Jun. 21, 2001, now abandoned.

(51) Int. Cl.
C07H 21/02 (2006.01)
C07H 21/04 (2006.01)

(52) U.S. Cl. .................... 536/24.5; 536/23.1; 536/24.3; 536/24.33

(58) Field of Classification Search ................ 536/23.1, 536/24.3, 24.33, 24.5
See application file for complete search history.

(56) References Cited

U.S. PATENT DOCUMENTS

| | | |
|---|---|---|
| 5,536,638 A | 7/1996 | Rossau et al. |
| 5,801,154 A | 9/1998 | Baracchini et al. |
| 5,843,641 A | 12/1998 | Brown et al. |
| 5,849,290 A | 12/1998 | Brown et al. |
| 5,994,076 A | 11/1999 | Chenchik et al. |
| 5,998,148 A | 12/1999 | Bennett et al. |
| 6,077,833 A | 6/2000 | Bennett et al. |
| 6,194,150 B1 | 2/2001 | Stinchcomb et al. |
| 6,352,829 B1 | 3/2002 | Chenchik et al. |
| 6,582,908 B2 | 6/2003 | Fodor et al. |
| 6,784,290 B1 * | 8/2004 | Monia et al. ............... 536/24.5 |
| 7,132,530 B2 * | 11/2006 | Bennett et al. ............. 536/24.5 |
| 2001/0053519 A1 | 12/2001 | Fodor et al. |
| 2002/0156040 A1 | 10/2002 | Oberley et al. |
| 2003/0228597 A1 | 12/2003 | Cowsert et al. |
| 2005/0019915 A1 | 1/2005 | Bennett et al. |
| 2006/0229268 A1 | 10/2006 | Benjamin et al. |
| 2007/0054869 A1 | 3/2007 | Bennett et al. |
| 2007/0117772 A1 | 5/2007 | Bennett et al. |

FOREIGN PATENT DOCUMENTS

| | | |
|---|---|---|
| WO | WO 90/05181 A1 | 5/1990 |
| WO | WO 94/19493 A1 | 9/1994 |
| WO | WO 97/26270 A2 | 7/1997 |
| WO | WO 97/31012 A1 | 8/1997 |
| WO | WO 02/03979 A2 | 1/2002 |
| WO | WO 02/44321 | 6/2002 |
| WO | WO 03/000707 A3 | 1/2003 |
| WO | WO 03/004602 A2 | 1/2003 |
| WO | WO 2005/040180 A3 | 5/2005 |

OTHER PUBLICATIONS

Dean et al. Antisense oligonucleotide-based therapeutics for cancer. Oncogene, 2003 vol. 22:9087-9096.*
Hammond, S. M. et al., "Post-Transcriptional Gene Silencing by Double-Stranded RNA," *Nature* (2002) 2:110-119.
PCT International Search Report for PCT/US2004/031673 dated Aug. 22, 2005.
Al-Chalabi, L. et al., "Recent advances in amyotrophic lateral sclerosis," *Curr Opin Neurol.* (2000) 13(4):397-405.
Alisky, J.M. et al., "Gene therapy for amyotrophic lateral sclerosis and other motor neuron diseases," *Hum Gene Ther.* (2000) 11(17):2315-29.
Branch, A. D., "A good antisense molecule is hard to find," *TIBS* (1998) 23:45-50.
Bruijn, L. I., et al., "Aggregation and motor neuron toxicity of an ALS-linked SOD1 mutant independent from wild-type SOD1," *Science* (1998) 281(5384):1851-4.
Cleveland, D. W., et al., "Oxidation versus aggregation-how do SOD1 mutants cause ALS?" *Nat Med.* (2000) 6(12):1320-1.
Crooke, S.T."Basic Principles of Antisense Therapeutics," (1998), Chapter 1, Springer-Verlag, New York.
Fridovich, I., "Superoxide radical and superoxide dismutases," *Annu. Rev. Biochem.* (1995) 64:97-112.

(Continued)

*Primary Examiner*—Sean McGarry
*Assistant Examiner*—Terra Cotta Gibbs
(74) *Attorney, Agent, or Firm*—Jones Day

(57) ABSTRACT

Antisense compounds, compositions and methods are provided for modulating the expression of superoxide dismutase 1, soluble. The compositions comprise antisense compounds, particularly antisense oligonucleotides, targeted to nucleic acids encoding superoxide dismutase 1, soluble. Methods of using these compounds for modulation of superoxide dismutase 1, soluble expression and for treatment of diseases associated with expression of superoxide dismutase 1, soluble are provided.

34 Claims, 4 Drawing Sheets

OTHER PUBLICATIONS

Green, D. W., et al, "Antisense Oligonucleotides: An Evolving Technology for the Modulation of Gene Expression in Human Disease," *J Am Coll Surg.* (2000) 191(1):93-105.

Grzanna, R., et al, "Intrastriatal and intraventricular injections of oligodeoxynucleotides in the rat brain: tissue penetration, intracellular distribution and c-fos antisense effects," *Mol Brain Res.* (1998) 63(1):35-52.

Gulesserian, T., et al., "Superoxide Dimutase SOD 1, Encoded on Chromosome 21, but Not SOD2 Is Overexpressed in Brains of Patients With Down Syndrome," J. Investig Med. (2001) 49(1):41-6.

Hottinger, A. F., "The copper chelator d-penicillamine delays onset of disease and extends survival in a transgenic mouse model of familial amyotrophic lateral sclerosis," *Eur J Neurosci.* (1997) 9(7):1548-51.

Huang, P. et al., "Superoxide dismutase as a target for the selective killing of cancer cells," *Nature.* (2000) 407(6802):390-5.

Jen, K.Y., et al., "Suppression of Gene Expression by Targeted Disruption of Messenger RNA: Available Options and Current Strategies," *Stem Cells* (2000) 18:307-19.

Kawata, A., et al., "Aberrant splicing of human Cu/Zn superoxide dimutase (SOD1) RNA transcripts," *Neuroreport.* (2000) 11(12):2649-53.

Klivenyi, P., et al., "Neuroprotective effecs of creatine in a transgenic animal model of amyotrophic lateral sclerosis," *Nat Med.* (1999) 5(3):347-50.

Lee, W. G., et al., "Molecular Cloning and High-Level Expression of Human Cytoplasmic Superoxide Dismutase Gene in *Escherichia coli*," *Kor. Jour. Microbiol.* (1990) 28(2): 91-7.

Milner, N., et al., "Selecting effective antisense reagents on combinatorial oligonucleotide arrays," *Nature Biotechnology* (1997) 15:537-41.

Misra, A., et al, "Drug delivery to the central nervous system: a review," J Pharm Pharmaceut Sci (2003) 6(2):252-273.

Muramatsu, H., et al., "Superoxide Dismutase in SAS Human Tongue Carcinoma Cell Line Is a Factor Defining Invasiveness and Cell Motility," *Cancer Research* (1995) 55:6210-4.

Rothstein, J. D., et al, "Chronic inhibition of superoxide dismutase produces apoptotic death of spinal Neurons" *Proc Natl Acad Sci U S A.* (1994) 91(10):4155-9.

Rowland, L. P., "Six important themes in amyotrophic lateral sclerosis (ALS) research, 1999," *J. Neurol. Sci.* (2000) 180:2-6.

Trotti, D., et al., "SOD1 mutants linked to amyotrophic lateral sclerosis selectively inactivate a glial glutamate transporter," *Nat Neurosci.* (1999) 2(5):427-33.

Troy, C. M., et al., "Down-regulation of Cu/Zn superoxide dismutase leads to cell death via the nitric oxide-peroxynitrite pathway," *J Neurosci.* (1996) 16(1):253-61.

Troy, C. M., et al., "Down-regulation of copper/zinc superoxide dismutase causes apoptotic death in PC12 neuronal cells," *Proc Natl Acad Sci U S A.* (1994) 91(14):6384-7.

Agrawal, S., et al., "Antisense therapeutics: is it as simple as complementary base recognition?," *Mol. Medicine Today* (2000) 6:72-81.

Berger, I., et al., "Crystal structures of B-DNA with incorporated 2'-deoxy-2'-fluoro-arabino-furanosyl thymines: implications of conformational preorganization for duplex stability," Nucleic Acids Res. (1998) 26(10):2473-80.

Berger, M. et al., "Universal bases for hybridization, replication and chain termination," *Nucleic Acids Research* (2000) 28(15): 2911-2914.

Brooks, B.R. et al., "El Escorial revisited: revisited criteria for the diagnosis of amyotrophic lateral sclerosis," *ALS and Other Motor Neuron Disorders* (2000) 1:293-299.

Klug et al. *European Journal of Physiology.* (2001) 441(6): R205. Abstract No. P20-7.

Sanghvi, Y.S., "Heterocyclic Base Modifications in Nucleic Acids and Their Applications in antisense Oligonucleotides," *Antisense Research and Applications* (1993) CRC Press, Boca Raton, pp. 276-278.

Skerra, A., "Phosphorothioate primers improve the amplification of DNA sequences by DNA polymerases with proofreading activity," *Nucleic Acids Research* (1992) 29(14):3551-4.

Office Action from U.S. Appl. No. 10/672,866, mail date May 3, 2005.

Office Action from U.S. Appl. No. 09/888,360, mail date May 21, 2002.

Final Rejection from U.S. Appl. No. 09/888,360, mail date Feb. 11, 2003.

Office Action from U.S. Appl. No. 10/633,843, mail date Nov. 15, 2005.

Final Rejection from U.S. Appl. No. 10/633,843, mail date Apr. 5, 2006.

Notice of Allowance from U.S. Appl. No. 10/633,843, mail date Jul. 3, 2006.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

New England BioLabs, Inc. Catalogue (1998): 121, 284.

Amorfix Life Sciences Ltd. "Amorfix Life Sciences Discovers Common Link Between ALS and Alzheimer's Disease" Press Release, Nov. 27, 2007.

Braasch et al., "Novel Antisense and Peptide Nucleic Acid Strategies for Controlling Gene Expression" Biochemistry (2002) 41(14):4503-4510.

Kagiyama et al., "Antisense inhibition of angiotensinogen attenuates vasopressin release in the paraventricular hypothalamic nucleus of spontaneously hypertensive rats" Brain Research (1999) 829:120-124.

Reynolds et al., "Rational siRNA design for RNA interference" Nature Biotechnology (2004) 22:326-330.

Scanlon, "Anti-Genes: siRNA, Ribozymes and Antisense" Current Pharmaceutical Biotechnology (2004) 5:415-420.

Sinnayaii et al., "Effects of angiotensinogen antisense oligonucleotides on fluid intake in response to different dipsogenic stimuli in the rat" Molecular Brain Research (1997) 50:43-50.

Smith et al., "Antisense oligonucleotide therapy for neurodegenerative disease" Journal of Clinical Investigation (2006) 116(8):2290-2296.

PCT International Search Report for PCT/US2002/19664 (RTSP-0384) dated Jan. 14, 2003.

Partial European Search Report for Application EP 02742241 (RTSP-0384EP) dated Nov. 08, 2004.

\* cited by examiner

ANTISENSE MODULATION OF SUPEROXIDE DISMUTASE 1, SOLUBLE EXPRESSION

RELATED APPLICATIONS

This application is a continuation of U.S. application Ser. No. 10/672,866, filed Sep. 26, 2003, now abandoned, which is a continuation-in-part of U.S. application Ser. No. 10/633,843, filed Aug. 4, 2003, now U.S. Pat. No. 7,132,530, which is a continuation of U.S. application Ser. No. 09/888,360, filed Jun. 21, 2001, now abandoned. The entire contents of these priority documents are incorporated herein by reference.

FIELD OF THE INVENTION

The present invention provides compositions and methods for modulating the expression of superoxide dismutase 1, soluble. In particular, this invention relates to compounds, particularly oligonucleotides, specifically hybridizable with nucleic acids encoding superoxide dismutase 1, soluble. Such compounds have been shown to modulate the expression of superoxide dismutase 1, soluble.

BACKGROUND OF THE INVENTION

The superoxide anion ($O_2^-$) is a potentially harmful cellular by-product produced primarily by errors of oxidative phosphorylation in mitochondria (Cleveland and Liu, *Nat. Med.*, 2000, 6, 1320-1321). Some of the targets for oxidation by superoxide in biological systems include the iron-sulfur dehydratases, aconitase and fumarases. Release of Fe(II) from these superoxide-inactivated enzymes results in Fenton-type production of hydroxyl radicals which are capable of attacking virtually any cellular target, most notably DNA (Fridovich, *Annu. Rev. Biochem.*, 1995, 64, 97-112).

The enzymes known as the superoxide dismutases (SODs) provide defense against oxidative damage of biomolecules by catalyzing the dismutation of superoxide to hydrogen peroxide ($H_2O_2$) (Fridovich, *Annu. Rev. Biochem.*, 1995, 64, 97-112). Two major classes of superoxide dismutases exist. One consists of a group of enzymes with active sites containing copper and zinc while the other class has either manganese or iron at the active site (Fridovich, *Annu. Rev. Biochem.*, 1995, 64, 97-112).

The soluble superoxide dismutase 1 enzyme (also known as SOD1 and Cu/Zn superoxide dismutase) contains a zinc- and copper-type active site (Fridovich, *Annu. Rev. Biochem.*, 1995, 64, 97-112). Lee et al. reported the molecular cloning and high-level expression of human cytoplasmic superoxide dismutase gene in *E. coli* in 1990 (Lee et al., *Misaengmul Hakhoechi*, 1990, 28, 91-97).

Mutations in the superoxide dismutase 1 gene are associated with a dominantly-inherited form of amyotrophic lateral sclerosis (ALS, also known as Lou Gehrig's disease) a disorder characterized by a selective degeneration of upper and lower motor neurons (Cleveland and Liu, *Nat. Med.*, 2000, 6, 1320-1321). The deleterious effects of various mutations on superoxide dismutase 1 are most likely mediated through a gain of toxic function rather than a loss of superoxide dismutase 1 activity, as the complete absence of superoxide dismutase 1 in mice neither diminishes life nor provokes overt disease (Al-Chalabi and Leigh, *Curr. Opin. Neurol.*, 2000, 13, 397-405; Alisky and Davidson, *Hum. Gene Ther.*, 2000, 11, 2315-2329).

According to Cleveland and Liu, there are two models for mutant superoxide dismutase 1 toxicity (Cleveland and Liu, *Nat. Med.*, 2000, 6, 1320-1321). The "oxidative hypothesis" ascribes toxicity to binding of aberrant substrates such as peroxynitrite or hydrogen peroxide which gain access to the catalytic copper ion through mutation-dependent loosening of the native superoxide dismutase 1 protein conformation (Cleveland and Liu, *Nat. Med.*, 2000, 6, 1320-1321). A second possible mechanism for mutant superoxide dismutase 1 toxicity involves the misfolding and aggregation of mutant superoxide dismutase 1 proteins (Cleveland and Liu, *Nat. Med.*, 2000, 6, 1320-1321). The idea that aggregates contribute to ALS has received major support from the observation that murine models of superoxide dismutase 1 mutant-mediated disease feature prominent intracellular inclusions in motor neurons and, in some cases, in the astrocytes surrounding them as well (Bruijn et al., *Science*, 1998, 281, 1851-1854). Furthermore, Brujin et al. also demonstrate that neither elimination nor elevation of wild-type superoxide dismutase 1 was found to affect disease induced by mutant superoxide dismutase 1 in mice (Bruijn et al., *Science*, 1998, 281, 1851-1854).

The superoxide dismutase 1 gene is localized to chromosome 21q22.1 and has been found to be overexpressed in the brains of patients with Down syndrome, possibly as a reflection of the trisomic state of chromosome 21 (Gulesserian et al., *J. Investig. Med.*, 2001, 49, 41-46).

Studies of transgenic mice carrying a mutant human superoxide dismutase 1 gene have been used to evaluate potential therapies for ALS and one such study has indicated that creatine produced a dose-dependent improvement in motor performance and extended survival in mice containing the glycine 93 to alanine mutation (Klivenyi et al., *Nat. Med.*, 1999, 5, 347-350). Although creatine is currently suggested as a dietary supplement for patients with ALS, the protective effect of creatine in humans has yet to be confirmed (Rowland, *J. Neurol. Sci.*, 2000, 180, 2-6).

Additional transgenic mice studies have led to the finding that oxidative reactions triggered by superoxide dismutase 1 mutants result in inactivation of the glial glutamate transporter (Human GLUT1) which in turn, causes neuronal degeneration (Trotti et al., *Nat. Neurosci.*, 1999, 2, 427-433).

Inhibition of superoxide dismutase 1 through copper chelation or zinc supplementation extends the life of mice that overexpress a mutant form superoxide dismutase by 1 to 2 months (Hottinger et al., *Eur. J. Neurosci.*, 1997, 9, 1548-1551). As reviewed by Alisky and Davidson, a number of pharmacological agents have been used to inhibit the toxicity of superoxide dismutase 1 mutants in the transgenic mouse model for human ALS, including: vitamin E, riluzole, gabapentin, caspase inhibitors, nitric oxide synthase inhibitors, glutamate receptor inhibitors and glutathione (Alisky and Davidson, *Hum. Gene Ther.*, 2000, 11, 2315-2329). In addition, investigational gene therapy for ALS has included overexpression of a number of genes which provide protection from superoxide dismutase 1 mutant toxicity (Alisky and Davidson, *Hum. Gene Ther.*, 2000, 11, 2315-2329).

Two abnormal superoxide dismutase 1 mRNAs, exon 2-skipping and exon 2 and 3-skipping species, were identified from occipital brain tissue of ALS patients carrying no mutations in the superoxide dismutase 1 gene (Kawata et al., *NeuroReport*, 2000, 11, 2649-2653).

Disclosed and claimed in PCT publication WO 94/19493 are oligonucleotide sequences encoding SOD1 and generally claimed is the use of an antisense DNA homolog of a gene encoding SOD1 in either mutant and wild-type forms in the preparation of a medicament for treating a patient with a disease (Brown et al., 1994).

The expression of superoxide dismutase 1 in PC12 rat pheochromocytoma neuronal cells was inhibited by either of two 1-mer antisense oligonucleotides targeting rat superoxide dismutase 1 nucleotides 54-74 and 497-517, leading to cellular apoptosis. The progression of cellular death was reversed by treatment with antioxidants (Troy and Shelanski, *Proc. Natl. Acad. Sci. U.S.A.*, 1994, 91, 6384-6387).

The method of delivery of the previously described oligonucleotides to the rat PC12 cells (Troy and Shelanski, *Proc. Natl. Acad. Sci. U.S.A.*, 1994, 91, 6384-6387) was subsequently improved by linking the oligonucleotides to a vector peptide via a disulfide bond (Troy et al., *J. Neurosci.*, 1996, 16, 253-261).

Induction of apoptosis was also seen in studies using a 30-mer phosphorothioate oligonucleotide targeting the start codon of superoxide dismutase 1 in rat spinal cord cultures in vitro (Rothstein et al., *Proc. Natl. Acad. Sci. U.S.A.*, 1994, 91, 4155-4159). Mutations of the superoxide dismutase 1 gene have been unambiguously implicated in ALS. However, investigational therapies involving inhibition of these mutants have yet to be tested as therapeutic protocols. Furthermore, evidence suggests that inhibition of the wild-type superoxide dismutase gene is not deleterious to organisms (Bruijn et al., *Science*, 1998, 281, 1851-1854). Consequently there remains a long felt need for agents capable of effectively and selectively inhibiting superoxide dismutase 1 function.

Antisense technology is emerging as an effective means for reducing the expression of specific gene products and may therefore prove to be uniquely useful in a number of therapeutic, diagnostic, and research applications for the modulation of superoxide dismutase 1 expression.

The present invention provides compositions and methods for modulating human superoxide dismutase 1 expression, including modulation of alternatively spliced forms of superoxide dismutase 1.

SUMMARY OF THE INVENTION

The present invention is directed to compounds, particularly antisense oligonucleotides, which are targeted to a nucleic acid encoding superoxide dismutase 1, soluble, and which modulate the expression of superoxide dismutase 1, soluble. Pharmaceutical and other compositions comprising the compounds of the invention are also provided. Further provided are methods of modulating the expression of superoxide dismutase 1, soluble in cells or tissues comprising contacting said cells or tissues with one or more of the antisense compounds or compositions of the invention. Further provided are methods of treating an animal, particularly a human, suspected of having or being prone to a disease or condition associated with expression of superoxide dismutase 1, soluble by administering a therapeutically or prophylactically effective amount of one or more of the antisense compounds or compositions of the invention.

DETAILED DESCRIPTION OF THE INVENTION

Figure 1:
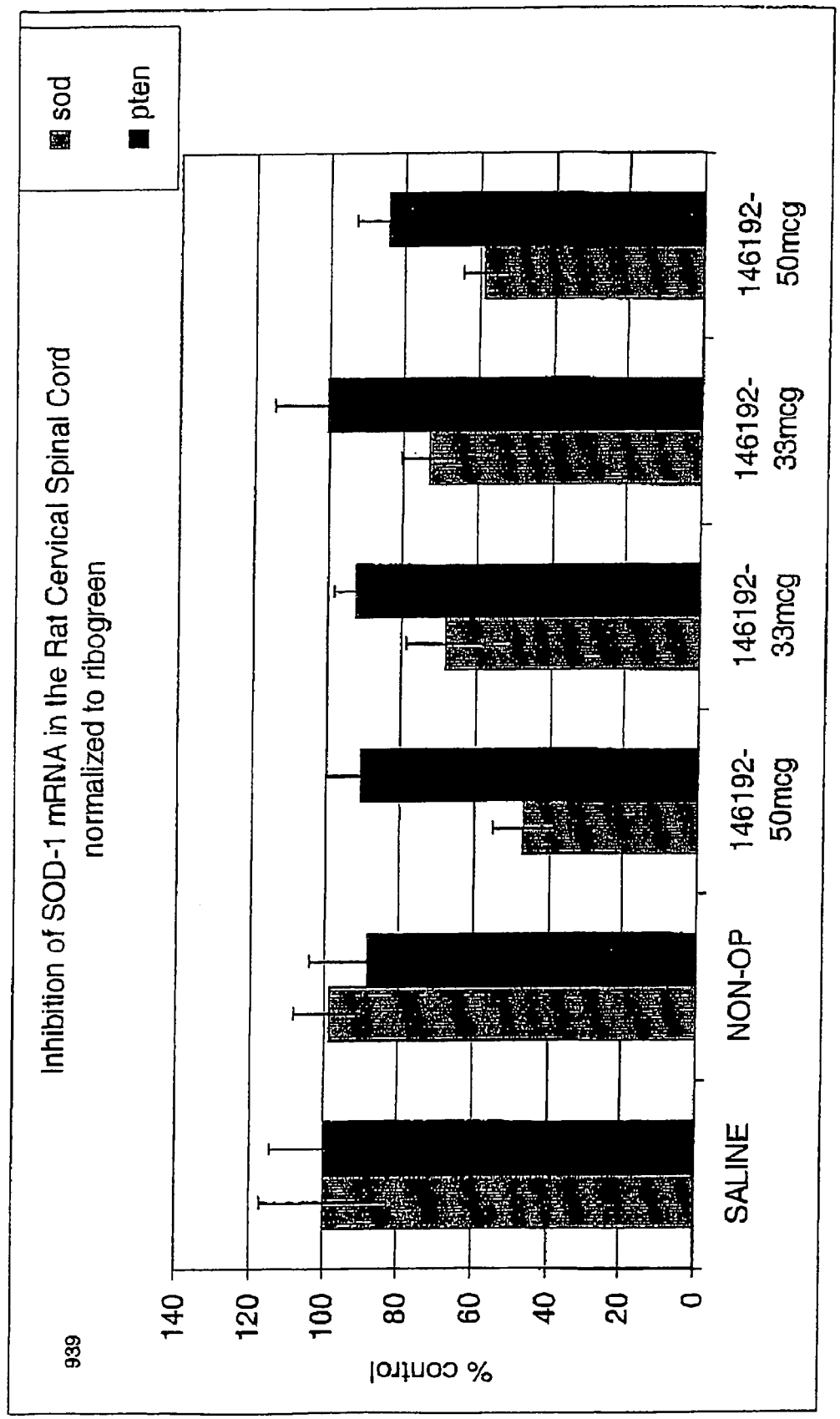
FIG. 1 is a bar graph showing inhibition of superoxide dismutase 1, soluble (SOD-1) mRNA in the rat cervical spinal cord after intraventricular administration of ISIS 146192, a SOD-1 antisense oligonucleotide. Sod=SOD-1. PTEN was used to show that ISIS 146192 is specific for SOD-1 and does not decrease levels of PTEN mRNA. mRNA levels were normalized to ribogreen.

The present invention employs oligomeric compounds, particularly antisense oligonucleotides, for use in modulating the function of nucleic acid molecules encoding superoxide dismutase 1, soluble, ultimately modulating the amount of superoxide dismutase 1, soluble produced. This is accomplished by providing antisense compounds which specifically hybridize with one or more nucleic acids encoding superoxide dismutase 1, soluble. As used herein, the terms "target nucleic acid" and "nucleic acid encoding superoxide dismutase 1, soluble" encompass DNA encoding superoxide dismutase 1, soluble, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of superoxide dismutase 1, soluble. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding superoxide dismutase 1, soluble. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding superoxide dismutase 1, soluble, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (reviewed in (To, *Comb. Chem. High Throughput Screen*, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697). The use of these double stranded RNA molecules (short interfering RNA or siRNA) for targeting and inhibiting the expression of superoxide dismutase 1, soluble mRNA is also contemplated. These double stranded RNA molecules target regions similar to those targeted by antisense oligocleotides and have similar effects. These double stranded RNA molecules are generally 19-21 base pairs in length, but may range between 8 and 50 nucleobases. The production of siRNA molecules is described in a general sense in the examples provided below, but it will be appreciated that any desired siRNA targeted to superoxide-1 dismutase, soluble may be synthesized by conventional oligonucleotide synthesis techniques. Once the sequence of the antisense strand is known, the complementary sense strand is synthesized based on base pairing. The sense and antisense strands are then combined to form the siRNA.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

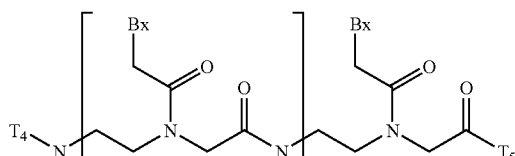

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

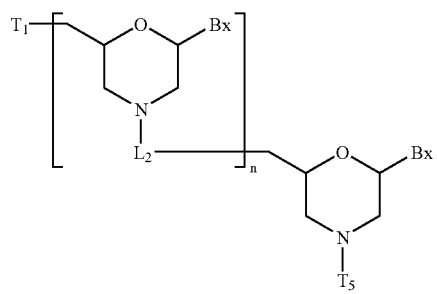

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

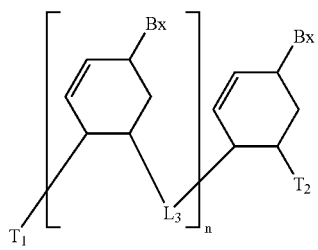

wherein each Bx is a heterocyclic base moiety;

$T_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

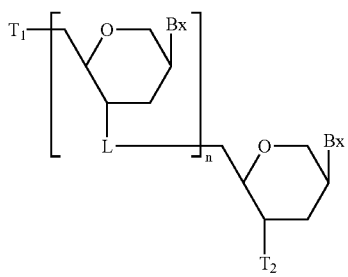

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene (—$CH_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

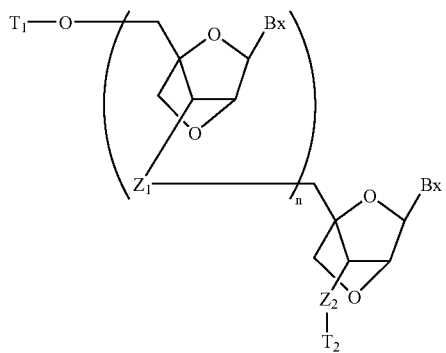

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

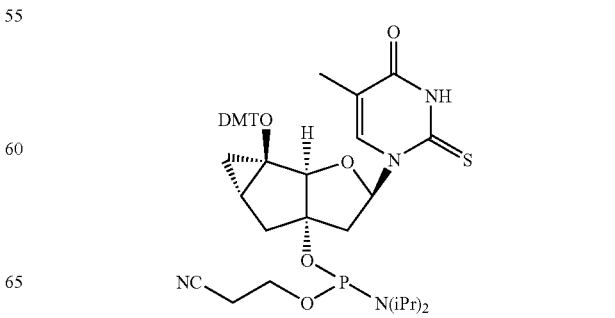

-continued

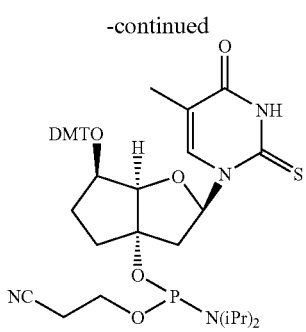

(see Steffens et al., *Helv. Chim. Acta,* 1997, 80, 2426-2439; Steffens et al., *J. Am. Chem. Soc.,* 1999, 121, 3249-3255; and Renneberg et al., *J. Am. Chem. Soc.,* 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

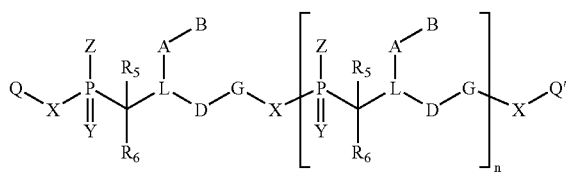

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

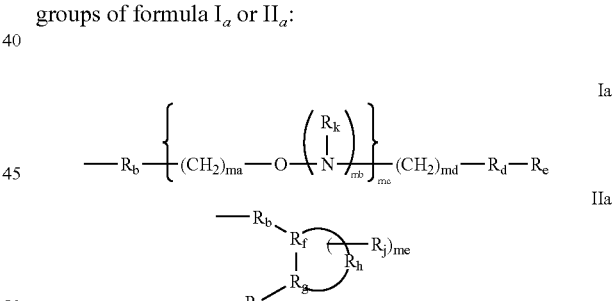

wherein:
$R_b$ is O, S or NH;
$R_d$ is a single bond, O, S or C(=O);
$R_e$ is $C_1$-$C_{10}$ alkyl, $N(R_k)(R_m)$, $N(R_k)(R_n)$, N=$C(R_p)(R_q)$, N=$C(R_p)(R_r)$ or has formula $III_a$;

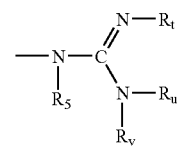

IIIa $R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

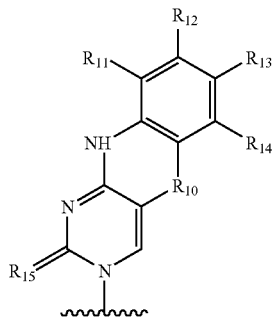

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions(also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocylcic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N. Y Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013, 830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Scheme 1

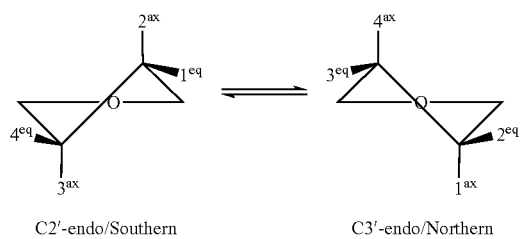

C2'-endo/Southern    C3'-endo/Northern

Figure 2:
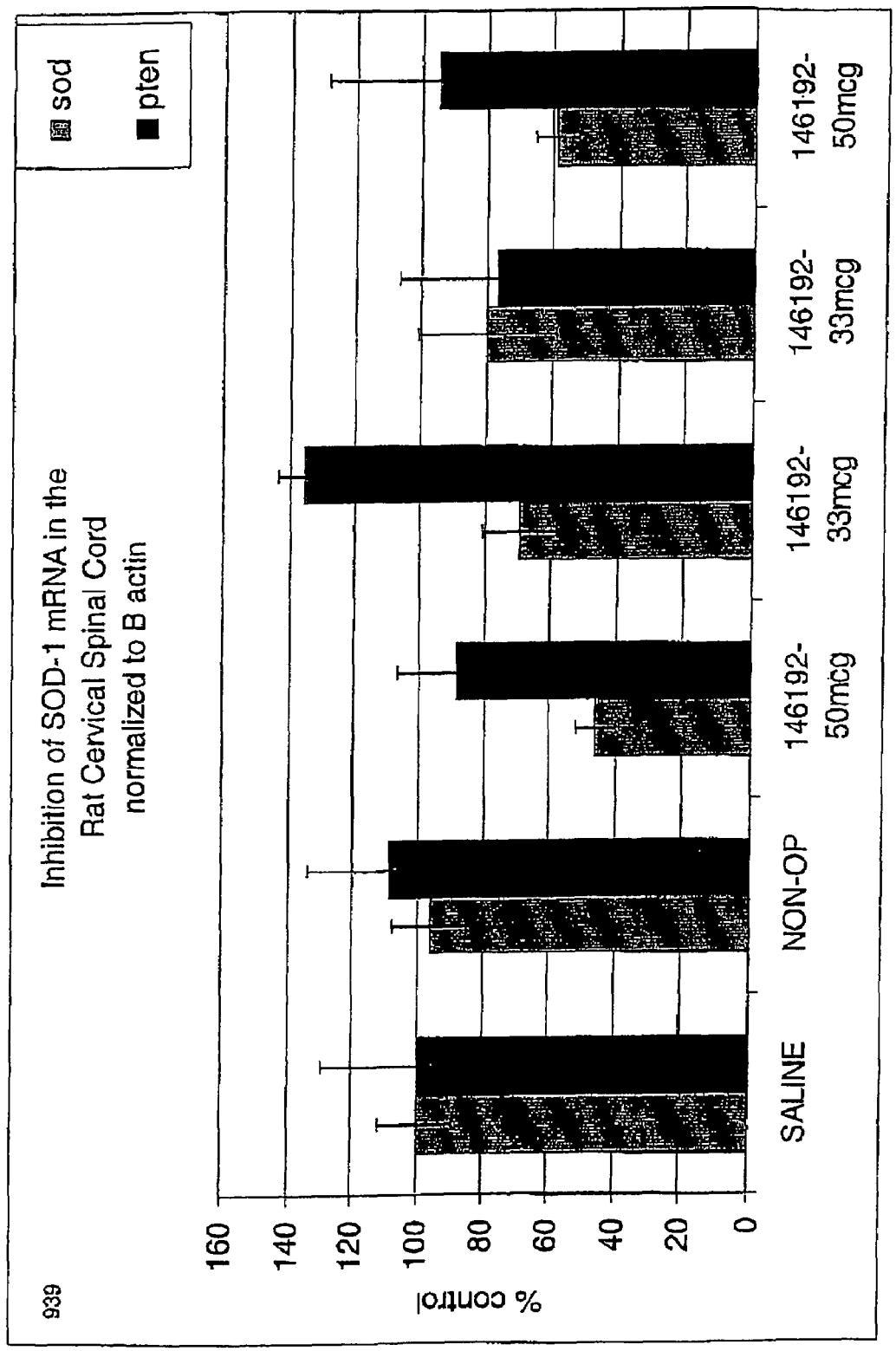
FIG. 2 is a bar graph showing inhibition of SOD-1 mRNA in the rat cervical spinal cord after intraventricular administration of ISIS 146192. mRNA levels were normalized to β-actin.
Figure 3:
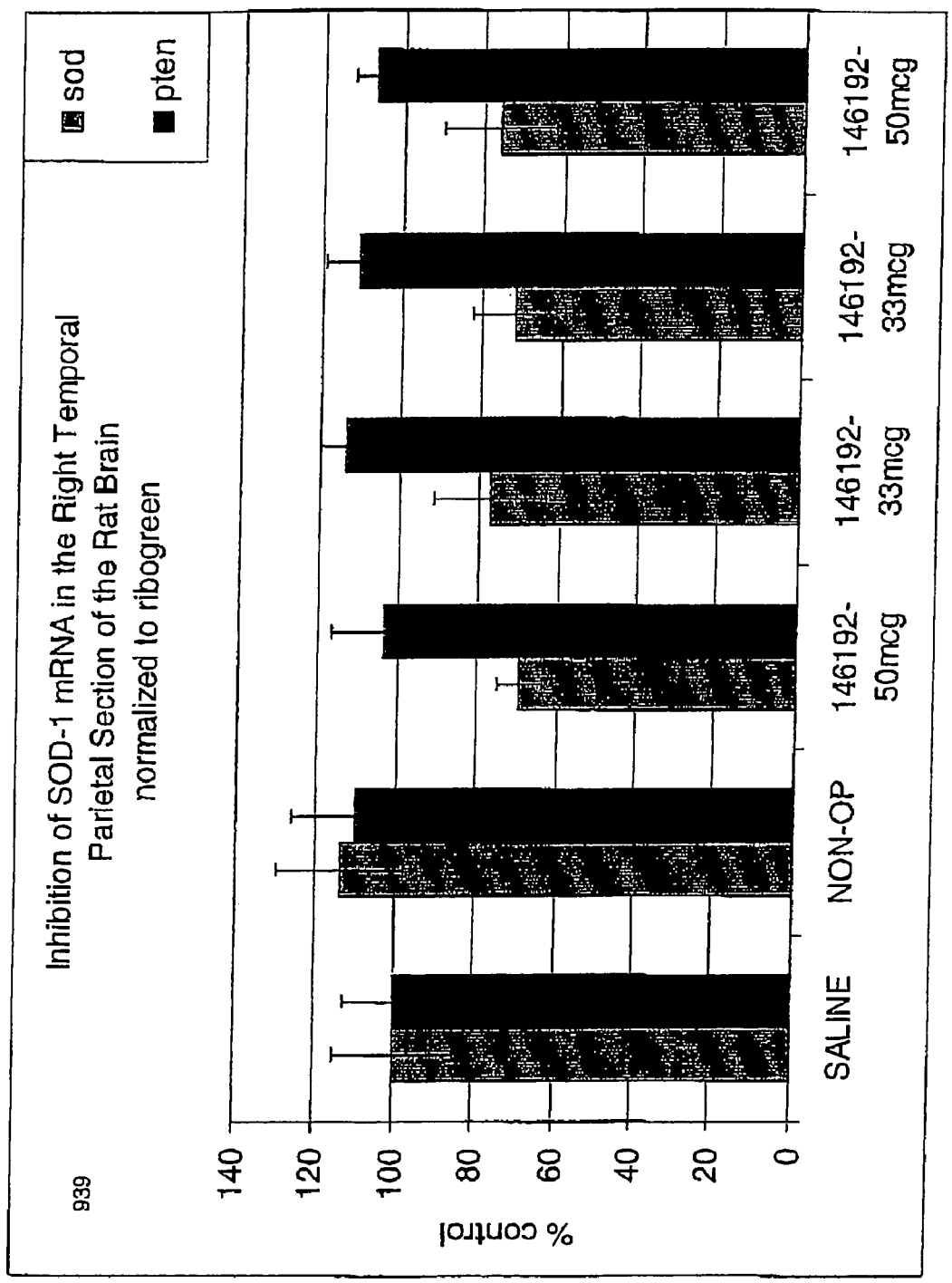
FIG. 3 is a bar graph showing inhibition of SOD-1 mRNA in the right temporal parietal section of the rat brain after intraventricular administration of ISIS 146192. mRNA levels were normalized to ribogreen.
Figure 4:
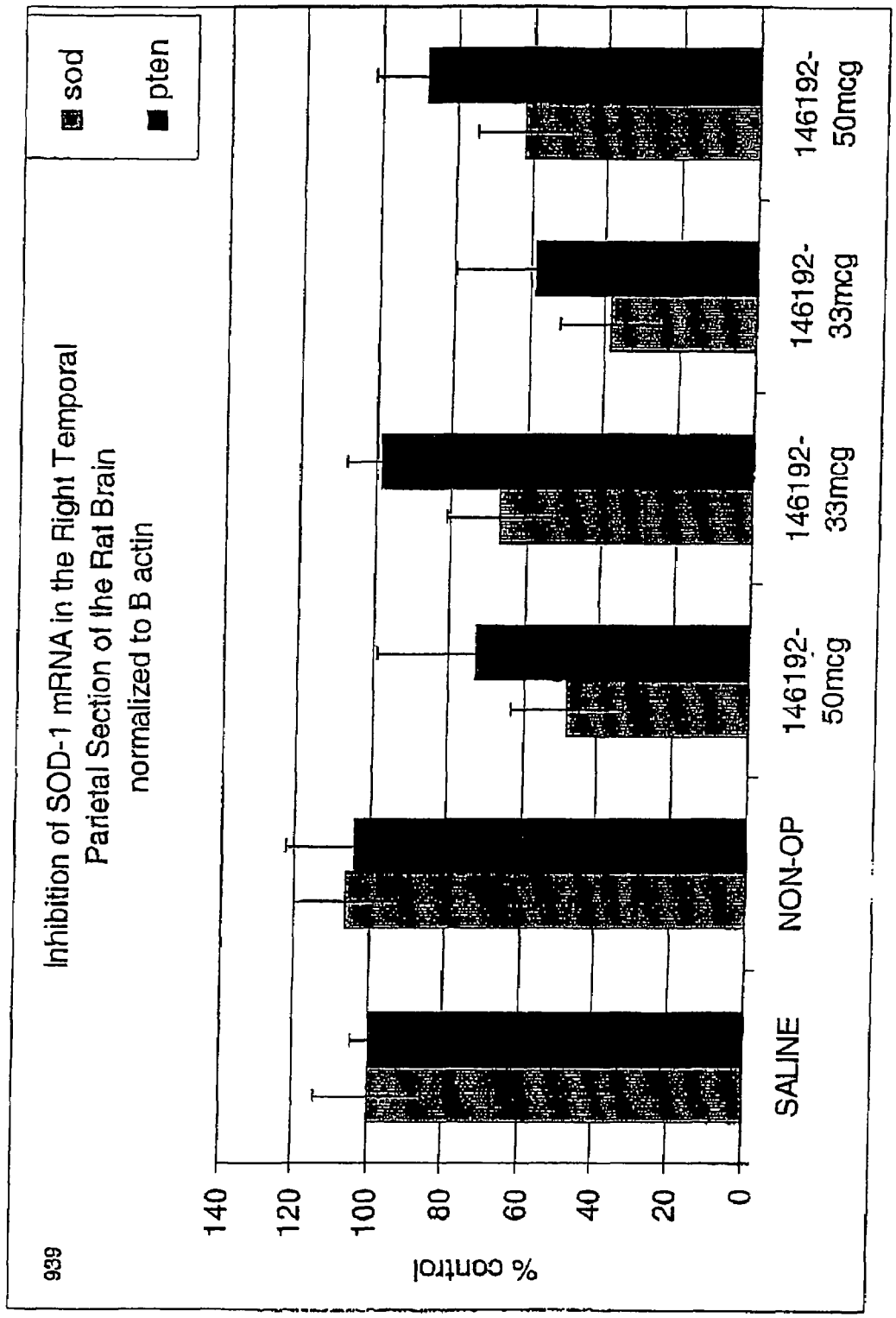
FIG. 4 is a bar graph showing inhibition of SOD-1 mRNA in the right temporal parietal section of the rat brain after intraventricular administration of ISIS 146192. mRNA levels were normalized to β-actin.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

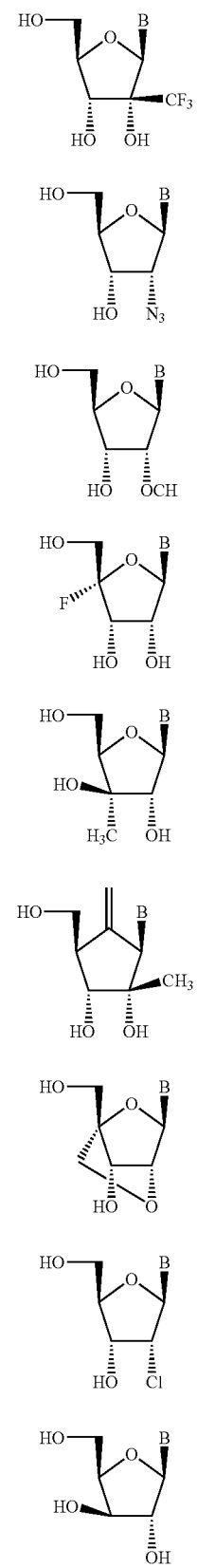

TABLE I-continued

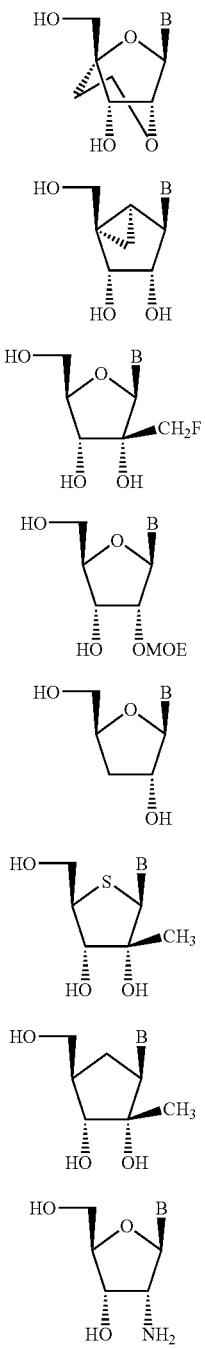

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research,* 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in 2 5 an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S. Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I. The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc. In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

The oligonucleotides in accordance with this invention (single stranded or double stranded) preferably comprise from about 8 to about 80 nucleotides, more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of superoxide dismutase-1, soluble mRNA.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of superoxide dismutase 1, soluble is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding superoxide dismutase 1, soluble, enabling sandwich and other assays to easily be constructed to exploit this fact. Hybridization of the antisense oligonucleotides of the invention with a nucleic acid encoding superoxide dismutase 1, soluble can be detected by means known in the art. Such means may include conjugation of an enzyme to the oligonucleotide, radiolabelling of the oligonucleotide or any other suitable detection means. Kits using such detection means for detecting the level of superoxide dismutase 1, soluble in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315, 298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates; polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N. Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p. 92); and perfluorochemical emulsions, such as FC43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p. 92; Muranishi, *Critical Reviews in Therapeutic Drug Carrier Systems,* 1990, 7, 1-33; El Hariri et al., *J. Pharm. Pharmacol.,* 1992, 44, 651-654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, N.Y., 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1-33; Yamamoto et al., *J. Pharm. Exp. Ther.,* 1992, 263, 25; Yamashita et al., *J. Pharm. Sci.,* 1990, 79, 579-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1-33; Buur et al., *J. Control Rel.,* 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1-33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115-121; Takakura et al., *Antisense & Nucl. Acid Drug Dev.*, 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis

Deoxy and 2'-alkoxy amidites

2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197-3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.*, 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the TIP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486-504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MEOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 ml) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in
DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1)

containing 0.5% Et₃NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra (isopropyl)-phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl)nucleoside amidites and 2'-O-(dimethylaminooxyethyl)nucleoside amidites

2'-(Dimethylaminooxyethoxy)nucleoside amidites

2'-(Dimethylaminooxyethoxy)nucleoside amidites [also known in the art as 2'-O-(dimethylaminooxyethyl)nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsflyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-[2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy)nucleoside amidites

2'-(Aminooxyethoxy)nucleoside amidites [also known in the art as 2'-O-(aminooxyethyl)nucleoside amidites] are prepared as described in the following paragraphs. Adenosine, cytidine and thymidine nucleoside amidites are prepared similarly.

N2-isobutyryl-6O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl)diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethyl-aminoethoxyethyl, i.e., 2'-O—$CH_2$—O—$CH_2$—N($CH_3$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL)

and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N, N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)]Chimeric Phosphorothioate Oligonucleotides

[2'-O-(2-methoxyethyl)]--[2'-deoxy]--[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl)Phosphodiester]Chimeric Oligonucleotides

[2'-O-(2-methoxyethyl phosphodiester]--[2'-deoxy phosphorothioate]--[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 16

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multichannel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Superoxide Dismutase 1, Soluble Expression Antisense modulation of superoxide dismutase 1, soluble expression can be assayed in a variety of ways known in the art. For example, superoxide dismutase 1, soluble mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of superoxide dismutase 1, soluble can be quantitated in a variety of ways well known in the art, such as immunoprecipitation, Western blot analysis (immunoblotting), ELISA or fluorescence-activated cell sorting (FACS). Antibodies directed to superoxide dismutase 1, soluble can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758-1764. Other methods for poly (A)+mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Superoxide Dismutase 1, Soluble mRNA Levels Quantitation of superoxide dismutase 1, soluble mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368-374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human superoxide dismutase 1, soluble were designed to hybridize to a human superoxide dismutase 1, soluble sequence, using published sequence information (GenBank accession number X02317, incorporated herein as SEQ ID NO:3). For human superoxide dismutase 1, soluble the PCR primers were:

```
forward primer:
CGTGGCCTAGCGAGTTATGG             (SEQ ID NO: 4)

reverse primer:
GAAATTGATGATGCCCTGCA             (SEQ ID NO: 5)

and the PCR probe was:
FAM-ACGAAGGCCGTGTGCGTGCTG-TAMRA  (SEQ ID NO: 6)
``` where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

```
forward primer:
GAAGGTGAAGGTCGGAGTC              (SEQ ID NO: 7)

reverse primer:
GAAGATGGTGATGGGATTTC             (SEQ ID NO: 8)

and the PCR probe was:
5' JOE-CAAGCTTCCCGTTCTCAGCC-TAMRA 3' (SEQ ID NO: 9)
``` where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Superoxide Dismutase 1, Soluble mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by WV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human superoxide dismutase 1, soluble, a human superoxide dismutase 1, soluble specific probe was prepared by PCR using the forward primer CGTGGCCTAGCGAGTTATGG (SEQ ID NO: 4) and the reverse primer GAAATTGATGATGCCCTGCA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Superoxide Dismutase 1, Soluble Expression by Chimeric Phosphorothioate Oligonucleotides Having 2'-MOE Wings and a Deoxy Gap In accordance with the present invention, a series of oligonucleotides was designed to target different regions of the human superoxide dismutase 1, soluble RNA, using published sequences (GenBank accession number X02317, incorporated herein as SEQ ID NO: 3, genomic sequence representing residues 15001-26000 of GenBank accession number AP000213.1, incorporated herein as SEQ ID NO: 10, GenBank accession number AI085992, an EST suggesting a splice variant of superoxide dismutase 1, soluble lacking exon 2, the complement of which is incorporated herein as SEQ ID NO: 11, and GenBank accession number N28535 which extends SEQ ID NO:3 in the 5' direction, incorporated herein as SEQ ID NO: 12). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human superoxide dismutase 1, soluble mRNA levels by quantitative real-time PCR as described in other examples herein. Data are averages from two experiments. If present, "N.D." indicates "no data".

TABLE 1

Inhibition of human superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146143 | Coding | 3 | 73 | tcagcacgcacacggccttc | 95 | 13 |
| 146144 | Coding | 3 | 78 | gcccttcagcacgcacacgg | 0 | 14 |

TABLE 1-continued

Inhibition of human superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146145 | Coding | 3 | 81 | gtcgcccttcagcacgcaca | 97 | 15 |
| 150437 | 5'UTR | 3 | 14 | cgaggactgcaacggaaacc | 0 | 16 |
| 150438 | 5'UTR | 3 | 19 | ggttccgaggactgcaacgg | 87 | 17 |
| 150439 | 5'UTR | 3 | 23 | tcctggttccgaggactgca | 84 | 18 |
| 150440 | 5'UTR | 3 | 27 | gaggtcctggttccgaggac | 0 | 19 |
| 150441 | 5'UTR | 3 | 38 | taggccacgccgaggtcctg | 84 | 20 |
| 150442 | Start Codon | 3 | 53 | gtcgccataactcgctaggc | 4 | 21 |
| 150443 | Coding | 3 | 96 | gccctgcactgggccgtcgc | 94 | 22 |
| 150444 | Coding | 3 | 106 | aattgatgatgccctgcact | 62 | 23 |
| 150445 | Coding | 3 | 135 | cactggtccattactttcct | 91 | 24 |
| 150446 | Coding | 3 | 142 | acaccttcactggtccatta | 93 | 25 |
| 150447 | Coding | 3 | 144 | ccacaccttcactggtccat | 0 | 26 |
| 150448 | Coding | 3 | 161 | agtcctttaatgcttcccca | 86 | 27 |
| 150449 | Coding | 3 | 173 | aggccttcagtcagtccttt | 29 | 28 |
| 150450 | Coding | 3 | 174 | caggccttcagtcagtcctt | 90 | 29 |
| 150451 | Coding | 3 | 205 | tatctccaaactcatgaaca | 68 | 30 |
| 150452 | Coding | 3 | 212 | gctgtattatctccaaactc | 90 | 31 |
| 150453 | Coding | 3 | 221 | gtacagcctgctgtattatc | 69 | 32 |
| 150454 | Coding | 3 | 304 | tgcccaagtctccaacatgc | 89 | 33 |
| 150455 | Coding | 3 | 309 | cacattgcccaagtctccaa | 22 | 34 |
| 150456 | Coding | 3 | 335 | tcggccacaccatctttgtc | 85 | 35 |
| 150457 | Coding | 3 | 337 | catcggccacaccatctttg | 94 | 36 |
| 150458 | Coding | 3 | 340 | acacatcggccacaccatct | 86 | 37 |
| 150459 | Coding | 3 | 343 | tagacacatcggccacacca | 87 | 38 |
| 150460 | Coding | 3 | 404 | accaccagtgtgcggccaat | 21 | 39 |
| 150461 | Coding | 3 | 409 | catggaccaccagtgtgcgg | 75 | 40 |
| 150462 | Coding | 3 | 410 | tcatggaccaccagtgtgcg | 59 | 41 |
| 150463 | Coding | 3 | 504 | ggcgatcccaattacaccac | 94 | 42 |
| 150464 | Stop Codon | 3 | 517 | ggaatgtttattgggcgatc | 91 | 43 |
| 150465 | 3'UTR | 3 | 535 | cctcagactacatccaaggg | 37 | 44 |
| 150466 | 3'UTR | 3 | 556 | gataacagatgagttaaggg | 61 | 45 |
| 150467 | 3'UTR | 3 | 620 | cacaattacactttttaagat | 21 | 46 |
| 150468 | 3'UTR | 3 | 625 | agtcacacaattacactttt | 0 | 47 |
| 150469 | 3'UTR | 3 | 658 | ctcactacaggtactttaaa | 50 | 48 |
| 150470 | 3'UTR | 3 | 667 | aatcagtttctcactacagg | 0 | 49 |
| 150471 | 3'UTR | 3 | 670 | ataaatcagtttctcactac | 46 | 50 |
| 150472 | 3'UTR | 3 | 671 | cataaatcagtttctcacta | 47 | 51 |
| 150473 | 3'UTR | 3 | 686 | aatcttccaagtgatcataa | 55 | 52 |
| 150474 | 3'UTR | 3 | 691 | atacaaatcttccaagtgat | 48 | 53 |
| 150475 | 3'UTR | 3 | 707 | tgagttttataaaactatac | 2 | 54 |
| 150476 | 3'UTR | 3 | 710 | aactgagttttataaaacta | 23 | 55 |
| 150477 | 3'UTR | 3 | 721 | acagacattttaactgagtt | 49 | 56 |
| 150478 | 3'UTR | 3 | 727 | attgaaacagacattttaac | 45 | 57 |
| 150479 | 3'UTR | 3 | 729 | tcattgaaacagacatttta | 41 | 58 |
| 150480 | 3'UTR | 3 | 736 | atacaggtcattgaaacaga | 66 | 59 |
| 150481 | 3'UTR | 3 | 761 | ccatctgtgatttaagtctg | 58 | 60 |
| 150482 | 3'UTR | 3 | 769 | tttaatacccatctgtgatt | 50 | 61 |
| 150483 | 3'UTR | 3 | 771 | agtttaatacccatctgtga | 43 | 62 |
| 150484 | 3'UTR | 3 | 787 | caaagaaattctgacaagtt | 44 | 63 |
| 150485 | 3'UTR | 3 | 795 | ttgaatgacaaagaaattct | 3 | 64 |
| 150486 | 3'UTR | 3 | 801 | acaggcttgaatgacaaaga | 0 | 65 |
| 150487 | 3'UTR | 3 | 805 | attcacaggcttgaatgaca | 0 | 66 |
| 150488 | 3'UTR | 3 | 812 | ggttttattcacaggcttg | 53 | 67 |
| 150489 | 3'UTR | 3 | 814 | agggttttattcacaggct | 34 | 68 |
| 150490 | 3'UTR | 3 | 818 | atacagggttttattcaca | 63 | 69 |
| 150491 | 3'UTR | 3 | 820 | ccatacagggttttattca | 44 | 70 |
| 150492 | 3'UTR | 3 | 825 | aagtgccatacagggttttt | 40 | 71 |
| 150493 | 3'UTR | 3 | 829 | taataagtgccatacagggt | 27 | 72 |
| 150494 | 3'UTR | 3 | 832 | tcataataagtgccatacag | 0 | 73 |
| 150495 | 3'UTR | 3 | 833 | ctcataataagtgccataca | 52 | 74 |
| 150496 | 3'UTR | 3 | 835 | gcctcataataagtgccata | 47 | 75 |
| 150497 | 3'UTR | 3 | 843 | ttttaatagcctcataataa | 31 | 76 |
| 150498 | 3'UTR | 3 | 849 | ggattcttttaatagcctca | 38 | 77 |
| 150499 | Intron: Exon Junction | 10 | 790 | cagcccttgccttctgctcg | 86 | 78 |
| 150500 | Intron 1 | 10 | 3845 | agtagctgggactacaggcg | 0 | 79 |

TABLE 1-continued

Inhibition of human superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 150501 | Intron 1 | 10 | 4738 | cattactttcctttaagaaa | 63 | 80 |
| 150502 | Intron 2 | 10 | 6248 | aagatcactaaatgcaactt | 57 | 81 |
| 150503 | Intron 2 | 10 | 7023 | caggagaatcgcttgaacct | 9 | 82 |
| 150504 | Intron: Exon Junction | 10 | 7397 | ctggtacagcctatttataa | 65 | 83 |
| 150505 | Intron 3 | 10 | 8053 | gcttcacgtctacacactaa | 28 | 84 |
| 150506 | Intron: Exon Junction | 10 | 8206 | tccaacatgcctaataatga | 36 | 85 |
| 150507 | mRNA | 11 | 30 | tggtacagccttctgctcga | 0 | 86 |
| 150508 | 5'UTR | 12 | 20 | taggccagacctccgcgcct | 0 | 87 |
| 150509 | 5'UTR | 12 | 26 | actttataggccagacctcc | 0 | 88 |
| 150510 | 5'UTR | 12 | 56 | gacgcaaaccagcaccccgt | 29 | 89 |
| 150511 | 5'UTR | 12 | 73 | acgctgcaggagactacgac | 81 | 90 |

As shown in Table 1, SEQ ID NOs 13, 15, 17, 18, 20, 22, 23, 24, 25, 27, 29, 30, 31, 32, 33, 35, 36, 37, 38, 40, 41, 42, 43, 45, 48, 52, 59, 60, 61, 67, 69, 74, 78, 80, 81, 83 and 90 demonstrated at least 50% inhibition of human superoxide dismutase 1, soluble expression in this assay and are therefore preferred. The target sites to which these preferred sequences are complementary are herein referred to as "active sites" and are therefore preferred sites for targeting by compounds of the present invention.

Example 16

Western Blot Analysis of Superoxide Dismutase 1, Soluble Protein Levels

Western blot analysis (immunoblot analysis) was carried out using standard methods. Cells (A549 and rat A10) were harvested 16-20 h after oligonucleotidetreatment, washed once with PBS, suspended in Laemmli buffer (100 ul/well), boiled for 5 minutes and loaded on a 16% SDS-PAGE gel. Superoxide dismutase 1, soluble oligonucleotides used were ISIS 146144 and ISIS 146145. A scrambled superoxide dismutase 1, soluble oligonucleotide was used as a negative control, as were cells not treated with oligonucleotide (untreated control). Gels are run for 1.5 hours at 150 V, and transferred to membrane for western blotting. Appropriate primary antibody directed to superoxide dismutase 1, soluble was used, with a radiolabelled or fluorescently labeled secondary antibody directed against the primary antibody species. Bands were visualized using a PHOSPHORIMAGER™ (Molecular Dynamics, Sunnyvale Calif.). ISIS 146144 and 146145 each inhibited production of superoxide dismutase 1, soluble by >75%, while the scrambled control oligonucleotide had no effect on levels superoxide dismutase 1, soluble. The untreated control cells also showed no reduction in levels of superoxide dismutase 1, soluble.

Example 17

Chimeric Phosphorothioate Oligonucleotides Targeted to Human Superoxide Dismutase 1, Soluble Having 2'-MOE Wings and a Deoxy Gap In accordance with the present invention, a second series of oligonucleotides was designed to target different regions of the human superoxide dismutase 1, soluble RNA, using published sequences (GenBank accession number X02317, incorporated herein as SEQ ID NO: 3). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 2

Chimeric phosphorothioate oligonucleotides targeted to human superoxide dismutase 1, soluble having 2'-MOE wings and a deoxy gap

| ISIS # | REGION | TARGET SEQ ID NO | TARGET SITE | SEQUENCE | SEQ ID NO |
|---|---|---|---|---|---|
| 331678 | start | 3 | 66 | GCACACGGCCTTCGTCGCCA | 91 |
| 333605 | coding | 3 | 74 | TTCAGCACGCACACGGCCTT | 92 |
| 333606 | coding | 3 | 76 | CCTTCAGCACGCACACGGCC | 93 |
| 333607 | coding | 3 | 77 | CCCTTCAGCACGCACACGGC | 94 |
| 333608 | coding | 3 | 79 | CGCCCTTCAGCACGCACACG | 95 |
| 333609 | coding | 3 | 80 | TCGCCCTTCAGCACGCACAC | 96 |
| 333610 | coding | 3 | 82 | CGTCGCCCTTCAGCACGCAC | 97 |
| 333611 | coding | 3 | 83 | CCGTCGCCCTTCAGCACGCA | 98 |
| 333612 | coding | 3 | 292 | CAACATGCCTCTCTTCATCC | 99 |
| 333613 | coding | 3 | 293 | CCAACATGCCTCTCTTCATC | 100 |

TABLE 2-continued

Chimeric phosphorothioate oligonucleotides targeted to human superoxide dismutase 1, soluble having 2'-MOE wings and a deoxy gap

| ISIS # | REGION | TARGET SEQ ID NO | TARGET SITE | SEQUENCE | SEQ ID NO |
|---|---|---|---|---|---|
| 333614 | coding | 3 | 294 | TCCAACATGCCTCTCTTCAT | 101 |
| 333615 | coding | 3 | 295 | CTCCAACATGCCTCTCTTCA | 102 |
| 333616 | coding | 3 | 296 | TCTCCAACATGCCTCTCTTC | 103 |
| 333617 | coding | 3 | 297 | GTCTCCAACATGCCTCTCTT | 104 |
| 333618 | coding | 3 | 373 | CTCCTGAGAGTGAGATCACA | 105 |
| 333619 | coding | 3 | 374 | TCTCCTGAGAGTGAGATCAC | 106 |
| 333620 | coding | 3 | 436 | CACCTTTGCCCAAGTCATCT | 107 |
| 333621 | coding | 3 | 437 | CCACCTTTGCCCAAGTCATC | 108 |
| 333622 | coding | 3 | 438 | TCCACCTTTGCCCAAGTCAT | 109 |
| 333623 | coding | 3 | 439 | TTCCACCTTTGCCCAAGTCA | 110 |
| 333625 | coding | 3 | 441 | ATTTCCACCTTTGCCCAAGT | 111 |
| 333626 | coding | 3 | 442 | CATTTCCACCTTTGCCCAAG | 112 |
| 333627 | coding | 3 | 443 | TCATTTCCACCTTTGCCCAA | 113 |
| 333628 | coding | 3 | 444 | TTCATTTCCACCTTTGCCCA | 114 |
| 333629 | coding | 3 | 445 | CTTCATTTCCACCTTTGCCC | 115 |
| 333630 | coding | 3 | 446 | TCTTCATTTCCACCTTTGCC | 116 |
| 333631 | coding | 3 | 447 | TTCTTCATTTCCACCTTTGC | 117 |
| 333632 | coding | 3 | 448 | TTTCTTCATTTCCACCTTTG | 118 |
| 333633 | coding | 3 | 449 | CTTTCTTCATTTCCACCTTT | 119 |
| 333634 | coding | 3 | 450 | ACTTTCTTCATTTCCACCTT | 120 |
| 333635 | coding | 3 | 451 | TACTTTCTTCATTTCCACCT | 121 |
| 333636 | coding | 3 | 452 | GTACTTTCTTCATTTCCACC | 122 |
| 333637 | coding | 3 | 453 | TGTACTTTCTTCATTTCCAC | 123 |
| 333638 | coding | 3 | 454 | TTGTACTTTCTTCATTTCCA | 124 |
| 333639 | coding | 3 | 455 | TTTGTACTTTCTTCATTTGC | 125 |
| 333640 | coding | 3 | 456 | CTTTGTACTTTCTTCATTTC | 126 |
| 333641 | coding | 3 | 457 | TCTTTGTACTTTCTTCATTT | 127 |
| 333642 | coding | 3 | 458 | GTCTTTGTACTTTCTTCATT | 128 |

Example 18

Phosphorothioate Oligodeoxynucleotides Targeted to Human Seperoxide Dismutase 1, Soluble In a further embodiment of the present invention, a third series of oligonucleotides was designed to target different regions of the human superoxide dismutase 1, soluble RNA, using published sequences (GenBank accession number X02317, incorporated herein as SEQ ID NO: 3; genomic sequence representing nucleotides 15001 to 26000 of GenBank accession number AP000213.1, incorporated herein as SEQ ID NO: 10). The oligonucleotides are shown in Table 3. "Target site" indicates the first (5'-most) nucleotide number on the particular target sequence to which the oligonucleotide binds. All compounds in Table 3 are oligodeoxynucleotides 20 nucleotides in length. The internucleoside (backbone) linkages are phosphorothioate (P=S) throughout the oligonucleotide. All cytidine residues are 5-methylcytidines.

TABLE 3

Phosphorothioate oligodeoxynucleotides targeted to human superoxide dismutase 1, soluble

| ISIS # | REGION | TARGET SEQ ID NO | TARGET SITE | SEQUENCE | SEQ ID NO |
|---|---|---|---|---|---|
| 336629 | coding | 3 | 127 | CATTACTTTCCTTCTGCTCG | 129 |
| 336631 | coding | 3 | 294 | TCCAACATGCCTCTCTTCAT | 130 |
| 336633 | intron:exon | 10 | 4738 | CATTACTTTCCTTTAAGAAA | 131 |
| 336635 | exon:intron | 10 | 4835 | CAACACCCACCTGCTGTATT | 132 |
| 336637 | intron | 10 | 7397 | CTGGTACAGCCTATTTATAA | 133 |
| 336639 | exon:intron | 10 | 7468 | CATCTTGTTACCTCTCTTCA | 134 |

TABLE 3-continued

Phosphorothioate oligodeoxynucleotides targeted to human superoxide dismutase 1, soluble

| ISIS # | REGION | TARGET SEQ ID NO | TARGET SITE | SEQUENCE | SEQ ID NO |
|---|---|---|---|---|---|
| 336641 | intron:exon | 10 | 8206 | TCCAACATGCCTAATAATGA | 135 |
| 336643 | exon | 10 | 8324 | GAAAACTTACCACCAGTGTG | 136 |
| 336645 | intron:exon | 10 | 9420 | TTTTCATGGACCTGTAAAAA | 137 |
| 336647 | 3'UTR | 3 | 849 | GGATTCTTTTAATAGCCTCA | 138 |

In addition to targeting human superoxide dismutase 1, soluble mRNA, SEQ ID NO: 130 also targets rat superoxide dismutase 1, soluble.

In a further embodiment of the present invention, a fourth series of oligonucleotides was designed to target different regions of the human superoxide dismutase 1, soluble RNA, using published sequences (GenBank accession number X02317, incorporated herein as SEQ ID NO: 3; genomic sequence representing nucleotides 15001 to 26000 of GenBank accession number AP000213.1, incorporated herein as SEQ ID NO: 10). The oligonucleotides are shown in Table 4. "Target site" indicates the first (5'-most) nucleotide number on the particular target sequence to which the oligonucleotide binds. All compounds in Table 4 are oligodeoxynucleotides 15 nucleotides in length. The internucleoside (backbone) linkages are phosphorothioate (P=S) throughout the oligonucleotide. All cytidine residues are 5-methylcytidines.

TABLE 4

Phosphorothioate oligodeoxynucleotides targeted to human superoxide dismutase 1, soluble

| ISIS # | REGION | TARGET SEQ ID NO | TARGET SITE | SEQUENCE | SEQ ID NO |
|---|---|---|---|---|---|
| 336630 | coding | 3 | 129 | TACTTTCCTTCTGCT | 139 |
| 336632 | coding | 3 | 296 | AACATGCCTCTCTTC | 140 |
| 336634 | intron:exon | 10 | 4740 | TACTTTCCTTTAAGA | 141 |
| 336636 | exon:intron | 10 | 4837 | CACCCACCTGCTGTA | 142 |
| 336638 | intron:exon | 10 | 7399 | GTACAGCCTATTTAT | 143 |
| 336640 | exon:intron | 10 | 7470 | CTTGTTACCTCTCTT | 144 |
| 336642 | intron | 10 | 8208 | AACATGCCTAATAAT | 145 |
| 336644 | exon:intron | 10 | 8326 | AACTTACCACCAGTG | 146 |
| 336646 | intron:exon | 10 | 9422 | TCATGGACCTGTAAA | 147 |
| 336648 | exon | 10 | 9858 | TTCTTTTAATAGCCT | 148 |

In addition to targeting human superoxide dismutase 1, soluble mRNA, SEQ ID NO: 140 also targets rat superoxide dismutase 1, soluble.

Example 19

Antisense Inhibition of Rat Superoxide Dismutase 1, Soluble Expression by Chimeric Phosphorothioate Oligonucleotides Having 2'-MOE Wings and a Deoxy Gap In accordance with the present invention, a series of oligonucleotides was designed to target different regions of the rat superoxide dismutase 1, soluble RNA, using published sequences (GenBank accession number Y00404.1, incorporated herein as SEQ ID NO: 149; GenBank accession number Z21917.1, incorporated herein as SEQ ID NO: 150; GenBank accession number Z21918.1, incorporated herein as SEQ ID NO: 151; GenBank accession number X54986. 1, incorporated herein as SEQ ID NO: 152; GenBank accession number Z21919.1, incorporated herein as SEQ ID NO: 153; GenBank accession number Z21920.1, incorporated herein as SEQ ID NO: 154; GenBank accession number Z21924.1, incorporated herein as SEQ ID NO: 155; GenBank accession number X55397.1, incorporated herein as SEQ ID NO: 156). The oligonucleotides are shown in Table 5. "Target site" indicates the first (5'-most) nucleotide number on the particular target sequence to which the oligonucleotide binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on rat superoxide dismutase 1, soluble in primary rat hepatocytes. Primary rat hepatocytes were prepared from Sprague-Dawley rats purchased from Charles River Labs (Wilmington, Mass.) and were routinely cultured in DMEM, high glucose (Gibco/Life Technologies, Gaithersburg, Md.) supplemented with 10% fetal bovine serum (Gibco/Life Technologies, Gaithersburg, Md.), 100 units per ml penicillin, and 100 micrograms per ml streptomycin (Gibco/Life Technologies, Gaithersburg, Md.).

Cells were seeded into 96-well plates (Falcon-Primaria #353047, BD Biosciences, Bedford, Mass.) at a density of 4000-6000 cells/well for use in antisense oligonucleotide transfection. For cells grown in 96-well plates, cells were treated with 100 uL of OPTI-MEM-1 containing 2.5 ug/mL LIPOFECTIN (Invitrogen Corporation, Carlsbad, Calif.) and the desired concentration of oligonucleotide. Cells were treated and data are obtained in triplicate. After 4 hours of treatment at 37° C., the medium was replaced with fresh medium. Cells were harvested 16-24 hours after oligonucleotide treatment.

ISIS 18078 was used as a control oligonucleotide. ISIS 18078 (GTGCGCGCGAGCCCGAAATC, SEQ ID NO: 157) is a chimeric oligonucleotide ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on rat superoxide dismutase 1, soluble mRNA levels in rat hepatocytes by quantitative real-time PCR as described in other examples herein. Probes and primers to mouse superoxide dismutase 1 were designed to hybridize to a rat superoxide dismutase 1, soluble sequence, using published sequence information (incorporated herein as SEQ ID NO: 149). For rat superoxide dismutase 1, soluble the PCR primers were: forward primer: TGCTGAAGGGCGACGG (SEQ ID NO: 159) reverse primer: GTTCACCGCTTGCCTTCTG (SEQ ID NO: 160) and the PCR probe was: FAM-CCGGTGCAGGGCGTCAT-TCACTT-TAMRA (SEQ ID NO: 161) where FAM is the fluorescent reporter dye and TAMRA is the quencher dye. Gene target quantities obtained by real time RT-PCR are normalized by quantifying total RNA using RiboGreen™ (Molecular Probes, Inc. Eugene, Oreg.). In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Data are averages from two experiments in which primary rat hepatocytes were treated with the antisense oligonucleotides of the present invention at a dose of 150 nM. If present, "N.D." indicates "no data".

TABLE 5

Inhibition of rat superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146137 | 5'UTR | 149 | 4 | CGCAGGAAACGAAGGTGCAA | 82 | 162 |
| 146138 | 5'UTR | 149 | 6 | GCCGCAGGAAACGAAGGTGC | 88 | 163 |
| 146139 | 5'UTR | 149 | 49 | CTCGGAACCTGGGAGAGCAA | 40 | 164 |
| 146140 | 5'UTR | 149 | 85 | TTCATCGCCATGCTTCCCCG | 79 | 165 |
| 146141 | 5'UTR | 149 | 91 | ACGGCCTTCATCGCCATGCT | 88 | 166 |
| 146142 | start | 149 | 94 | CACACGGCCTTCATCGCCAT | 79 | 167 |

TABLE 5-continued

Inhibition of rat superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146143 | coding | 149 | 102 | TCAGCACGCACACGGCCTTC | 83 | 168 |
| 146144 | coding | 149 | 107 | GCCCTTCAGCACGCACACGG | 95 | 169 |
| 146145 | coding | 149 | 110 | GTCGCCCTTCAGCACGCACA | 91 | 170 |
| 146146 | coding | 149 | 115 | GGACCGTCGCCCTTCAGCAC | 97 | 171 |
| 146147 | coding | 149 | 143 | CTGCTCGAAGTGAATGACGC | 97 | 172 |
| 146148 | coding | 149 | 151 | CTTGCCTTCTGCTCGAAGTG | 89 | 173 |
| 146149 | coding | 149 | 156 | CACCGCTTGCCTTCTGCTCG | 92 | 174 |
| 146150 | coding | 149 | 161 | TGGTTCACCGCTTGCCTTCT | 78 | 175 |
| 146151 | coding | 149 | 166 | ACAACTGGTTCACCGCTTGC | 90 | 176 |
| 146152 | coding | 149 | 183 | TAATCTGTCCTGACACCACA | 83 | 177 |
| 146153 | coding | 149 | 188 | TCCTGTAATCTGTCCTGACA | 84 | 178 |
| 146154 | coding | 149 | 192 | TTAATCCTGTAATCTGTCCT | 85 | 179 |
| 146155 | coding | 149 | 208 | CCATGCTCGCCTTCAGTTAA | 80 | 180 |
| 146156 | coding | 149 | 217 | ACATGGAACCCATGCTCGCC | 82 | 181 |
| 146157 | coding | 149 | 225 | ATTGATGGACATGGAACCCA | 87 | 182 |
| 146158 | coding | 149 | 244 | CCTTGTGTATTGTCCCCATA | 86 | 183 |
| 146159 | coding | 149 | 249 | TACAGCCTTGTGTATTGTCC | 77 | 184 |
| 146160 | coding | 149 | 278 | GTGAGGATTAAAATGAGGTC | 70 | 185 |
| 146161 | coding | 149 | 284 | CTTAGAGTGAGGATTAAAAT | 69 | 186 |
| 146162 | coding | 149 | 289 | TGTTTCTTAGAGTGAGGATT | 72 | 187 |
| 146163 | coding | 149 | 334 | TTGCCCAGGTCTCCAACATG | 79 | 188 |
| 146164 | coding | 149 | 337 | ACATTGCCCAGGTCTCCAAC | 78 | 189 |

TABLE 5-continued

Inhibition of rat superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146165 | coding | 149 | 359 | CACACCGTCCTTTCCAGCAG | 82 | 190 |
| 146166 | coding | 149 | 364 | TTGGCCACACCGTCCTTTCC | 82 | 191 |
| 146167 | coding | 149 | 367 | ACATTGGCCACACCGTCCTT | 74 | 192 |
| 146168 | coding | 149 | 369 | ACACATTGGCCACACCGTCC | 84 | 193 |
| 146169 | coding | 149 | 374 | AATGGACACATTGGCCACAC | 82 | 194 |
| 146170 | coding | 149 | 379 | TCTTCAATGGACACATTGGC | 78 | 195 |
| 146171 | coding | 149 | 384 | CACGATCTTCAATGGACACA | 86 | 196 |
| 146172 | coding | 149 | 387 | TCACACGATCTTCAATGAC | 76 | 197 |
| 146173 | coding | 149 | 389 | GATCACACGATCTTCAATGG | 88 | 198 |
| 146174 | coding | 149 | 421 | CGGCCAATGATGGAATGCTC | 85 | 199 |
| 146175 | coding | 149 | 426 | TAGTACGGCCAATGATGGAA | 87 | 200 |
| 146176 | coding | 149 | 439 | TCGTGGACCACCATAGTACG | 87 | 201 |
| 146177 | coding | 149 | 442 | TTCTCGTGGACCACCATAGT | 84 | 202 |
| 146178 | coding | 149 | 505 | CGGCTTCCAGCATTTCCAGT | 77 | 203 |
| 146179 | coding | 149 | 510 | CCAAGCGGCTTCCAGCATTT | 76 | 204 |
| 146180 | coding | 149 | 516 | CACAAGCCAAGCGGCTTCCA | 77 | 205 |
| 146181 | coding | 149 | 522 | TCACACCACAAGCCAAGCGG | 74 | 206 |
| 146182 | coding | 149 | 532 | GCAATCCCAATCACACCACA | 76 | 207 |
| 146183 | coding | 149 | 535 | TGGGCAATCCCAATCACACC | 82 | 208 |
| 146184 | coding | 149 | 539 | TTATTGGGCAATCCCAATCA | 87 | 209 |
| 146185 | coding | 149 | 553 | CACATAGGGAATGTTTATTG | 81 | 210 |
| 146186 | 3'UTR | 149 | 559 | TCAGACCACATAGGGAATGT | 71 | 211 |
| 146187 | 3'UTR | 149 | 563 | AGACTCAGACCACATAGGGA | 64 | 212 |
| 146188 | 3'UTR | 149 | 567 | TCTGAGACTCAGACCACATA | 83 | 213 |
| 146189 | 3'UTR | 149 | 583 | CAGGACAGCAGATGAGTCTG | 82 | 214 |
| 146190 | 3'UTR | 149 | 586 | TAGCAGGACAGCAGATGAGT | 89 | 215 |
| 146191 | 3'UTR | 149 | 592 | ACAGTTTAGCAGGACAGCAG | 90 | 216 |
| 146192 | 3'UTR | 149 | 595 | TCTACAGTTTAGCAGGACAG | 91 | 217 |
| 146193 | 3'UTR | 149 | 622 | GATTACAGTTTAATGGTTTG | 57 | 218 |
| 146194 | intron | 150 | 1996 | TAGCGATGCAAACTGCTCTC | 0 | 219 |
| 146195 | intron | 150 | 2002 | ATAGGATAGCGATGCAAACT | 38 | 220 |
| 146196 | exon:intron | 151 | 521 | TAGGACCTACCTTGTGTATT | 19 | 221 |
| 146197 | exon:intron | 152 | 235 | TAAGACTTACCTTGTGTATT | 11 | 222 |
| 146198 | intron | 152 | 280 | ACTCTGACCCATTCATCTCA | 55 | 223 |
| 146199 | exon:intron | 153 | 321 | GCTGCTCACCTCTCTTCATC | 52 | 224 |
| 146200 | intron | 153 | 594 | TTGCTAGTGACGTGATAGTA | 51 | 225 |
| 146201 | intron | 153 | 659 | ATACAAACGGAATCTCAACT | 57 | 226 |
| 146202 | intron | 153 | 714 | CTCCAGCTCATTCAAAGAGC | 21 | 227 |
| 146203 | intron | 153 | 743 | AGTATGCAGCTCCTGATTAC | 24 | 228 |
| 146204 | intron | 153 | 764 | GAAGGCACTTCGAGGTTACG | 45 | 229 |
| 146205 | exon:intron | 154 | 142 | GGAAACTTACCACCATAGTA | 46 | 230 |
| 146206 | exon:intron | 154 | 145 | TATGGAAACTTACCACCATA | 66 | 231 |
| 146207 | intron | 154 | 305 | GCAAATTAATTCTTTACTAT | 20 | 232 |
| 146208 | intron | 154 | 391 | GTATCCTCAACTCAGATCCA | 79 | 233 |

TABLE 5-continued

Inhibition of rat superoxide dismutase 1, soluble mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 146209 | intron: exon | 155 | 154 | TCTCGTGGACCTTTGAAAAG | 62 | 234 |
| 146210 | intron | 156 | 33 | AGCAGACTACTAAGTGTTTC | 44 | 235 |
| 146211 | intron | 156 | 52 | TTTTATGCTATCAGCTAAAA | 27 | 236 |
| 146212 | intron | 156 | 69 | TAAATCAATAAGCTAATTTT | 9 | 237 |
| 146213 | intron | 156 | 84 | GTTCAAATCTATTAGTAAAT | 36 | 238 |
| 146214 | intron: exon | 156 | 187 | CTCGTGGACCTTTGAAAAGA | 79 | 239 |

In addition to targeting rat superoxide dismutase 1, soluble mRNA, SEQ ID Nos 168, 169 and 170 also target human superoxide dismutase 1, soluble.

As shown in Table 5, SEQ ID Nos 162, 163, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 231, 233, 234 and 239 demonstrated at least 60% inhibition of rat superoxide dismutase 1, soluble expression in this assay and are therefore preferred. More preferred are SEQ ID NOs: 217, 216, and 215. The target sites to which these preferred sequences are complementary are herein referred to as "active sites" and are therefore preferred sites for targeting by compounds of the present invention.

Example 20

Chimeric Phosphorothioate Oligonucleotides Targeted to Rat Superoxide Dismutase 1, Soluble Having 2'-MOE Wings and a Deoxy Gap In a further embodiment of the present invention, a second series of oligonucleotides was designed to target different regions of the rat superoxide dismutase 1, soluble RNA, using published sequences (GenBank accession number Y00404.1, incorporated herein as SEQ ID NO: 149). The oligonucleotides are shown in Table 6. "Target site" indicates the first (5'-most) nucleotide number on the particular target sequence to which the oligonucleotide binds. All compounds in Table 6 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 6

Chimeric phosphorothioate oligonucleotides targeted to rat superoxide dismutase 1, soluble having 2'-MOE wings and a deoxy gap

| ISIS # | REGION | TARGET SEQ ID NO | TARGET SITE | SEQUENCE | SEQ ID NO |
|---|---|---|---|---|---|
| 195743 | 5'UTR | 149 | 40 | TGGGAGAGCAAAAAGCAAGG | 240 |
| 195744 | 5'UTR | 149 | 45 | GAACCTGGGAGAGCAAAAAG | 241 |
| 195745 | 5'UTR | 149 | 51 | GCCTCGGAACCTGGGAGAGC | 242 |
| 195746 | 5'UTR | 149 | 53 | CGGCCTCGGAACCTGGGAGA | 243 |
| 195747 | 5'UTR | 149 | 55 | GGCGGCCTCGGAACCTGGGA | 244 |
| 195748 | 5'UTR | 149 | 77 | CATGCTTCCCCGGGAGACGC | 245 |
| 195749 | 5'UTR | 149 | 81 | TCGCCATGCTTCCCCGGGAG | 246 |
| 195750 | 5'UTR | 149 | 83 | CATCGCCATGCTTCCCCGGG | 247 |
| 195751 | 5'UTR | 149 | 88 | GCCTTCATCGCCATGCTTCC | 248 |
| 195752 | coding | 149 | 99 | GCACGCACACGGCCTTCATC | 249 |
| 195753 | coding | 149 | 104 | CTTCAGCACGCACACGGCCT | 250 |
| 195754 | coding | 149 | 145 | TTCTGCTCGAAGTGAATGAC | 251 |
| 195755 | coding | 149 | 149 | TGCCTTCTGCTCGAAGTGAA | 252 |
| 195756 | coding | 149 | 153 | CGCTTGCCTTCTGCTCGAAG | 253 |
| 195757 | coding | 149 | 158 | TTCACCGCTTGCCTTCTGCT | 254 |
| 195758 | coding | 149 | 168 | CCACAACTGGTTCACCGCTT | 255 |
| 195759 | coding | 149 | 170 | CACCACAACTGGTTCACCGC | 256 |
| 195760 | coding | 149 | 178 | TGTCCTGACACCACAACTGG | 257 |
| 195761 | coding | 149 | 180 | TCTGTCCTGACACCACAACT | 258 |
| 195762 | coding | 149 | 185 | TGTAATCTGTCCTGACACCA | 259 |
| 195763 | coding | 149 | 190 | AATCCTGTAATCTGTCCTGA | 260 |
| 195764 | coding | 149 | 194 | AGTTAATCCTGTAATCTGTC | 261 |
| 195765 | coding | 149 | 196 | TCAGTTAATCCTGTAATCTG | 262 |
| 195766 | coding | 149 | 210 | ACCCATGCTCGCCTTCAGTT | 263 |

TABLE 6-continued

Chimeric phosphorothioate oligonucleotides targeted to rat superoxide dismutase 1, soluble having 2'-MOE wings and a deoxy gap

| ISIS # | REGION | TARGET SEQ ID NO | TARGET SITE | SEQUENCE | SEQ ID NO |
|---|---|---|---|---|---|
| 195767 | coding | 149 | 215 | ATGGAACCCATGCTCGCCTT | 264 |
| 195768 | coding | 149 | 219 | GGACATGGAACCCATGCTCG | 265 |
| 195769 | coding | 149 | 223 | TGATGGACATGGAACCCATG | 266 |
| 195770 | coding | 149 | 228 | CATATTGATGGACATGGAAC | 267 |
| 195771 | coding | 149 | 230 | CCCATATTGATGGACATGGA | 268 |
| 195772 | coding | 149 | 232 | TCCCCATATTGATGGACATG | 269 |
| 195773 | coding | 149 | 234 | TGTCCCCATATTGATGGACA | 270 |
| 195774 | coding | 149 | 236 | ATTGTCCCCATATTGATGGA | 271 |
| 195775 | coding | 149 | 241 | TGTGTATTGTCCCCATATTG | 272 |
| 195776 | coding | 149 | 246 | AGCCTTGTGTATTGTCCCCA | 273 |
| 195777 | coding | 149 | 286 | TTCTTAGAGTGAGGATTAAA | 274 |
| 195778 | coding | 149 | 291 | CATGTTTCTTAGAGTGAGGA | 275 |
| 195779 | coding | 149 | 293 | GCCATGTTTCTTAGAGTGAG | 276 |
| 195780 | coding | 149 | 297 | GACCGCCATGTTTCTTTAGAG | 277 |
| 195781 | coding | 149 | 299 | TGGACCGCCATGTTTCTTAG | 278 |
| 195782 | coding | 149 | 301 | GCTGGACCGCCATGTTTCTT | 279 |
| 195783 | coding | 149 | 303 | CCGCTGGACCGCCATGTTTC | 280 |
| 195784 | coding | 149 | 305 | ATCCGCTGGACCGCCATGTT | 281 |
| 195785 | coding | 149 | 307 | TCATCCGCTGGACCGCCATG | 282 |
| 195786 | coding | 149 | 309 | CTTCATCCGCTGGACCGCCA | 283 |
| 195787 | coding | 149 | 313 | CTCTCTTCATCCGCTGGACC | 284 |
| 195788 | coding | 149 | 315 | GCCTCTCTTCATCCGCTGGA | 285 |
| 195789 | coding | 149 | 339 | CCACATTGCCCAGGTCTCCA | 286 |
| 195790 | coding | 149 | 341 | AGCCACATTGCCCAGGTCTC | 287 |
| 195791 | coding | 149 | 353 | GTCCTTTCCAGCAGCCACAT | 288 |
| 195792 | coding | 149 | 356 | ACCGTCCTTTCCAGCAGCCA | 289 |
| 195793 | coding | 149 | 371 | GGACACATTGGCCACACCGT | 290 |
| 195794 | coding | 149 | 377 | TTCAATGGACACATTGGCCA | 291 |
| 195795 | coding | 149 | 423 | TACGGCCAATGATGGAATGC | 292 |
| 195796 | coding | 149 | 437 | GTGGACCACCATAGTACGGC | 293 |
| 195797 | coding | 149 | 503 | GCTTCCAGCATTTCCAGTCT | 294 |
| 195798 | coding | 149 | 512 | AGCCAAGGGGCTTCCAGCAT | 295 |
| 195799 | coding | 149 | 518 | ACCACAAGGCAAGCGGCTTC | 296 |
| 195800 | stop | 149 | 537 | ATTGGGCAATCCCAATCACA | 297 |
| 195801 | stop | 149 | 541 | GTTTATTGGGCAATCCCAAT | 298 |
| 195802 | stop | 149 | 555 | ACCACATAGGGAATGTTTAT | 299 |
| 195803 | stop | 149 | 557 | AGACCACATAGGGAATGTTT | 300 |
| 195804 | 3'UTR | 149 | 561 | ACTCAGACCACATAGGGAAT | 301 |
| 195805 | 3'UTR | 149 | 565 | TGAGACTCAGACCACATAGG | 302 |
| 195806 | 3'UTR | 149 | 571 | TGAGTCTGAGACTCAGACCA | 303 |
| 195807 | 3'UTR | 149 | 573 | GATGAGTCTGAGACTCAGAC | 304 |
| 195808 | 3'UTR | 149 | 575 | CAGATGAGTCTGAGACTCAG | 305 |
| 195809 | 3'UTR | 149 | 577 | AGCAGATGAGTCTGAGACTC | 306 |
| 195810 | 3'UTR | 149 | 581 | GGACAGCAGATGAGTCTGAG | 307 |
| 195811 | 3'UTR | 149 | 588 | TTTAGCAGGACAGCAGATGA | 308 |
| 195812 | 3'UTR | 149 | 590 | AGTTTAGCAGGACAGCAGAT | 309 |

TABLE 6-continued

Chimeric phosphorothioate oligonucleotides targeted to rat superoxide dismutase 1, soluble having 2'-MOE wings and a deoxy gap

| ISIS # | REGION | TARGET SEQ ID NO | TARGET SITE | SEQUENCE | SEQ ID NO |
|---|---|---|---|---|---|
| 195813 | 3'UTR | 149 | 597 | TTTCTACAGTTTAGCAGGAC | 310 |
| 195814 | 3'UTR | 149 | 599 | TTTTTCTACAGTTTAGCAGG | 311 |
| 195815 | 3'UTR | 149 | 626 | TTAAGATTACAGTTTAATGG | 312 |
| 195816 | 3'UTR | 149 | 628 | TGTTAAGATTACAGTTTAAT | 313 |
| 333624 | coding | 149 | 469 | TTTCCACCTTTGCCCAAGTC | 314 |

In addition to targeting rat superoxide dismutase 1, soluble mRNA, SEQ ID Nos 250 and 314 also target human superoxide dismutase 1, soluble.

In a further embodiment of the present invention, an oligonucleotide was designed to target the rat superoxide dismutase 1, soluble RNA, using published sequences (GenBank accession number Y00404.1, incorporated herein as SEQ ID NO: 149). This compound consists of the sequence CTTCAGCACGCACACGGC (SEQ ID NO: 315). This compound is a chimeric oligonucleotide ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The "target site", which indicates the first (5'-most) nucleotide number on the particular target sequence to which the oligonucleotide binds, is nucleotide 105 of SEQ ID NO: 149.

Example 21

Phosphorothioate Oligodeoxynucleotides Targeted to Rat Superoxide Dismutase 1, Soluble In a further embodiment of the present invention, a third series of oligonucleotides was designed to target different regions of the rat superoxide dismutase 1, soluble RNA, using published sequences (GenBank accession number Y00404.1, incorporated herein as SEQ ID NO: 149; GenBank accession number Z21924.1, incorporated herein as SEQ ID NO: 155; GenBank accession number Z21920.1, incorporated herein as SEQ ID NO: 154; GenBank accession number NM_017050.1, incorporated herein as SEQ ID NO: 316; genomic sequence representing nucleotides 5965000 to 5972000 of GenBank accession number NW_042743.1, incorporated herein as SEQ ID NO: 317). The oligonucleotides are shown in Table 7. "Target site" indicates the first (5'-most) nucleotide number on the particular target sequence to which the oligonucleotide binds. All compounds in Table 7 are oligodeoxynucleotides 20 nucleotides in length. The internucleoside (backbone) linkages are phosphorothioate (P=S) throughout the oligonucleotide. All cytidine residues are 5-methylcytidines.

TABLE 7

Phosphorothioate oligodeoxynucleotides targeted to rat superoxide dismutase 1, soluble

| ISIS # | REGION | TARGET SEQ ID NO | TARGET SITE | SEQUENCE | SEQ ID NO |
|---|---|---|---|---|---|
| 336649 | coding | 149 | 156 | CACCGCTTGCCTTCTGCTCG | 318 |
| 336651 | coding | 316 | 441 | TCTCGTGGACCACCATAGTA | 319 |
| 336653 | intron | 317 | 636 | TGCAAAACGAGGGCCCAGCG | 320 |
| 336655 | exon:intron | 317 | 802 | GGGCCTTGCCTTCTGCTCGA | 321 |
| 336657 | intron:exon | 317 | 2598 | CACCGCTTGCCTTTATTTAA | 322 |
| 336659 | exon:intron | 317 | 2696 | TTAAGACTTACCTTGTGTAT | 323 |
| 336661 | intron:exon | 317 | 4191 | GTGGTACAGCCTATTTACCA | 324 |
| 336663 | exon:intron | 317 | 4261 | TGCTGCTCACCTCTCTTCAT | 325 |
| 336665 | intron:exon | 317 | 4949 | TCCAACATGCCTAACATTAA | 326 |
| 336667 | exon:intron | 154 | 142 | GGAAACTTACCACCATAGTA | 327 |
| 336669 | intron | 154 | 154 | TCTCGTGGACCTTTGAAAAG | 328 |

In a further embodiment of the present invention, a third series of oligonucleotides was designed to target different regions of the rat superoxide dismutase 1, soluble RNA, using published sequences (GenBank accession number Y00404.1, incorporated herein as SEQ ID NO: 149; GenBank accession number Z21920.1, incorporated herein as SEQ ID NO: 154; GenBank accession number Z21924.1, incorporated herein as SEQ ID NO: 155; GenBank accession number NM_017050.1, incorporated herein as SEQ ID NO: 316; genomic sequence representing nucleotides 5965000 to 5972000 of GenBank accession number NW_042743.1, incorporated herein as SEQ ID NO: 317). The oligonucleotides are shown in Table 8. "Target site" indicates the first (5'-most) nucleotide number on the particular target sequence to which the oligonucleotide binds. All compounds in Table 8 are oligodeoxynucleotides 15 nucleotides in length. The internucleoside (backbone) linkages are phosphorothioate (P=S) throughout the oligonucleotide. All cytidine residues are 5-methylcytidines.

TABLE 8

Phosphorothioate oligodeoxynucleotides targeted to rat superoxide dismutase 1, soluble

| ISIS # | REGION | TARGET SEQ ID NO | TARGET SITE | SEQUENCE | SEQ ID NO |
|---|---|---|---|---|---|
| 336650 | coding | 316 | 158 | CGCTTGCCTTCTGCT | 329 |
| 336652 | coding | 316 | 443 | CGTGGACCACCATAG | 330 |

TABLE 8-continued

Phosphorothioate oligodeoxynucleotides targeted to rat superoxide dismutase 1, soluble

| ISIS # | REGION | TARGET SEQ ID NO | TARGET SITE | SEQUENCE | SEQ ID NO |
|---|---|---|---|---|---|
| 336654 | intron | 317 | 638 | AAAACGAGGGCCCAG | 331 |
| 336656 | exon:intron | 317 | 804 | CCTTGCCTTCTGCTC | 332 |
| 336658 | intron:exon | 317 | 2600 | CGCTTGCCTTTATTT | 333 |
| 336660 | exon:intron | 317 | 2698 | AGACTTACCTTGTGT | 334 |
| 336662 | intron:exon | 317 | 4193 | GTACAGCCTATTTAC | 335 |
| 336664 | exon:intron | 317 | 4263 | TGCTCACCTCTCTTC | 336 |
| 336666 | intron:exon | 317 | 4951 | AACATGCCTAACATT | 337 |
| 336668 | exon:intron | 317 | 5069 | AACTTACCACCATAG | 338 |
| 336670 | intron:exon | 317 | 6017 | CGTGGACCTTTGAAA | 339 |

In addition to targeting rat superoxide dismutase 1, soluble mRNA, SEQ ID NO: 130 also targets human superoxide dismutase 1, soluble.

Example 22

Inhibition of Superoxide Dismutase 1, Soluble mRNA in Rat Brain Following Intraventricular Administration Oligonucleotides that target the expression of proteins in the brain represent a potential means of treating degenerative neurologic disorders associated with aberrant proteins such as superoxide dismutase 1, soluble that are associated with familial ALS. To be effective in ALS, they would need to reach affected tissues.

Superoxide dismutase 1, soluble mRNA levels were measured in rat brain following intraventricular administration. Superoxide dismutase 1, soluble levels were measured in both rat spinal cord and rat brain following administration of ISIS 146192. Administration was performed daily at either 33 μg/day or 50 μg/day for 14 days. The results are shown in FIGS. 1-4. There are two sets of bars for each dose since duplicate treatment groups of 6 per group were used. Expression is relative to PTEN mRNA to demonstrate specificity. mRNA was normalized to ribogreen or beta-actin.

The results show that intraventricular administration of ISIS 146192 significantly reduced superoxide dismutase 1, soluble mRNA levels in both the spinal cord and right temporal parietal section of the brain. Thus, oligonucleotides are preferentially taken up by motor neurons in the brain stem and spinal cord, suggesting that cell barriers are not an obstacle. Thus, intraventricular administration of superoxide dismutase 1, soluble antisense oligonucleotides has therapeutic implications in treatment of ALS and other neurodegenerative disorders.

Example 23

Design and Screening of Duplexed Antisense Compounds Targeting Superoxide Dismutase-1, Soluble In accordance with the present invention, a series of nucleic acid duplexes comprising the antisense compounds of the present invention and their complements can be designed to target superoxide dismutase-1, soluble. The nucleobase sequence of the antisense strand of the duplex comprises at least a portion of an oligonucleotide to superoxide dismutase-1, soluble as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. For example, a duplex comprising an antisense strand having the sequence CGAGAGGCG-GACGGGACCG (SEQ ID NO: 342) and having a two-nucleobase overhang of deoxythymidine(dT) would have the following structure:

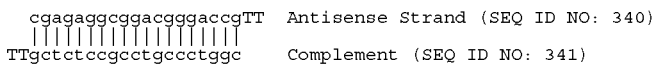
Antisense Strand (SEQ ID NO: 340)
Complement (SEQ ID NO: 341)

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate superoxide dismutase-1, soluble expression according to the protocols described herein.

Example 26

Design of Phenotypic Assays and in vivo Studies for the Use of Superoxide Dismutase-1, Soluble Inhibitors Phenotypic Assays Once superoxide dismutase-1, soluble inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association superoxide dismutase-1, soluble in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with superoxide dismutase-1, soluble inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest. Analysis of the genotype of the cell (measurement of the expression of one or more of the genes of the cell) after treatment is also used as an indicator of the efficacy or potency of superoxide dismutase-1, soluble inhibitors. Hallmark genes, or those genes suspected to be associated with a specific disease state, condition, or phenotype, are measured in both treated and untreated cells.

---

What is claimed is:

1. A compound 20 to 50 nucleobases in length comprising the nucleobase sequence of SEQ ID NO: 98.

2. The compound of claim 1 wherein the compound is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A compound consisting of the nucleobase sequence of SEQ ID NO: 98.

11. The compound of claim 10 wherein the compound is an antisense oligonucleotide.

12. The compound of claim 11 wherein the antisense oligonucleotide comprises at least one modified internucleoside linkage.

13. The compound of claim 12 wherein the modified internucleoside linkage is a phosphorothioate linkage.

14. The compound of claim 11 wherein the antisense oligonucleotide comprises at least one modified sugar moiety.

15. The compound of claim 14 wherein the modified sugar moiety is a 2'-O-methoxyethyl sugar moiety.

16. The compound of claim 11 wherein the antisense oligonucleotide comprises at least one modified nucleobase.

17. The compound of claim 16 wherein the modified nucleobase is a 5-methylcytosine.

18. The compound of claim 11 wherein the antisense oligonucleotide is a chimeric oligonucleotide.

19. The compound of claim 11 wherein nucleotides 1 to 5 and 16 to 20 have a 2'-O-methoxyethyl sugar moiety, each internucleoside linkage is a phosphorothioate linkage, and each cytosine is a 5-methylcytosine.

20. A compound comprising a modified oligonucleotide consisting of 12 to 30 linked nucleosides and having a nucleobase sequence comprising at least 12 contiguous nucleobases of the nucleobase sequence set forth in SEQ ID NO: 98.

21. The compound of claim 20, consisting of a single-stranded modified oligonucleotide.

22. The compound of claim 21, wherein the nucleobase sequence of the modified oligonucleotide is 100% complementary to SEQ ID NO: 3.

23. The compound of claim 21, wherein at least one internucleoside linkage is a modified internucleoside linkage.

24. The compound of claim 23, wherein each internucleoside linkage is a phosphorothioate internucleoside linkage.

25. The compound of claim 21, wherein at least one nucleoside comprises a modified sugar.

26. The compound of claim 25, wherein at least one modified sugar is a bicyclic sugar.

27. The compound of claim 25, wherein at least one modified sugar comprises a 2'-O-methoxyethyl.

28. The compound of claim 21, wherein at least one nucleoside comprises a modified nucleobase.

29. The compound of claim 28, wherein the modified nucleobase is a 5-methylcytosine.

30. The compound of claim 20, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

31. The compound of claim 30, wherein the gap segment consists of ten linked nucleosides and at least one internucleoside linkage is a phosphorothioate linkage.

32. The compound of claim 21, wherein the modified oligonucleotide consists of 20 linked nucleosides.

33. The compound of claim 32, wherein the modified oligonucleotide comprises:
   a gap segment consisting often linked deoxynucleosides;
   a 5' wing segment consisting of five linked nucleosides;
   a 3' wing segment consisting of five linked nucleosides;
   wherein the gap segment is positioned between the 5' wing segment and the 3' wing segment wherein each nucleoside of each wing segment comprises a 2'-O-methoxyethyl sugar; and wherein at least one intemucleoside linkage is a phosphorothioate linkage.

34. The compound of claim 33, wherein each internucleoside linkage is a phosphorotbioate linkage.

* * * * *

SEQUENCE LISTING

```
<160> NUMBER OF SEQ ID NOS: 342

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                               20

<210> SEQ ID NO 3
<211> LENGTH: 874
<212> TYPE: DNA
<213> ORGANISM: Homo sapiens
<220> FEATURE:
<220> FEATURE:
<221> NAME/KEY: CDS
<222> LOCATION: (65)...(529)

<400> SEQUENCE: 3
ctgcagcgtc tggggtttcc gttgcagtcc tcggaaccag gacctcggcg tggcctagcg      60 agtt atg gcg acg aag gcc gtg tgc gtg ctg aag ggc gac ggc cca gtg     109
     Met Ala Thr Lys Ala Val Cys Val Leu Lys Gly Asp Gly Pro Val
     1               5                  10                  15
```

```
cag ggc atc atc aat ttc gag cag aag gaa agt aat gga cca gtg aag      157
Gln Gly Ile Ile Asn Phe Glu Gln Lys Glu Ser Asn Gly Pro Val Lys
             20                  25                  30 gtg tgg gga agc att aaa gga ctg act gaa ggc ctg cat gga ttc cat      205
Val Trp Gly Ser Ile Lys Gly Leu Thr Glu Gly Leu His Gly Phe His
         35                  40                  45 gtt cat gag ttt gga gat aat aca gca ggc tgt acc agt gca ggt cct      253
Val His Glu Phe Gly Asp Asn Thr Ala Gly Cys Thr Ser Ala Gly Pro
     50                  55                  60 cac ttt aat cct cta tcc aga aaa cac ggt ggg cca aag gat gaa gag      301
His Phe Asn Pro Leu Ser Arg Lys His Gly Gly Pro Lys Asp Glu Glu
 65                  70                  75 agg cat gtt gga gac ttg ggc aat gtg act gct gac aaa gat ggt gtg      349
Arg His Val Gly Asp Leu Gly Asn Val Thr Ala Asp Lys Asp Gly Val
 80                  85                  90                  95 gcc gat gtg tct att gaa gat tct gtg atc tca ctc tca gga gac cat      397
Ala Asp Val Ser Ile Glu Asp Ser Val Ile Ser Leu Ser Gly Asp His
                100                 105                 110 tgc atc att ggc cgc aca ctg gtg gtc cat gaa aaa gca gat gac ttg      445
Cys Ile Ile Gly Arg Thr Leu Val Val His Glu Lys Ala Asp Asp Leu
            115                 120                 125 ggc aaa ggt gga aat gaa gaa agt aca aag aca gga aac gct gga agt      493
Gly Lys Gly Gly Asn Glu Glu Ser Thr Lys Thr Gly Asn Ala Gly Ser
        130                 135                 140 cgt ttg gct tgt ggt gta att ggg atc gcc caa taa acattccctt           539
Arg Leu Ala Cys Gly Val Ile Gly Ile Ala Gln
    145                 150             154 ggatgtagtc tgaggcccct taactcatct gttatcctgc tagctgtaga aatgtatcct    599
gataaacatt aaacactgta atcttaaaag tgtaattgtg tgacttttc agagttgctt     659 taaagtacct gtagtgagaa actgatttat gatcacttgg aagatttgta tagttttata    719
aaactcagtt aaaatgtctg tttcaatgac ctgtattttg ccagacttaa atcacagatg    779
ggtattaaac ttgtcagaat ttctttgtca ttcaagcctg tgaataaaaa ccctgtatgg    839
cacttattat gaggctatta aaagaatcca aattc                               874

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
cgtggcctag cgagttatgg                                                 20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
gaaattgatg atgccctgca                                                 20

<210> SEQ ID NO 6
<211> LENGTH: 21
<212> TYPE: DNA
<213> ORGANISM: Artificial Sequence
<220> FEATURE:
```

```
<223> OTHER INFORMATION: PCR Probe

<400> SEQUENCE: 6
acgaaggccg tgtgcgtgct g                                              21

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                20

<210> SEQ ID NO 10
<211> LENGTH: 11000
<212> TYPE: DNA
<213> ORGANISM: Homo sapiens
<220> FEATURE:

<400> SEQUENCE: 10
aaaaacgcag gtgatgccta gaagccaact agttgccgtt tggttatctg tagggttgtg      60
gccttgccaa acaggaaaaa tataaaaaga ataccgaatt ctgccaacca aataagaaac     120
tctatactaa ggactaagaa aattgcaggg gaagaaaagg taagtcccgg gattgaggtg     180
tagcgacttt ctatacccct agaaaactaa aaaacaagac aaaaaaatga aaactacaaa     240
agcatccatc ttggggcgtc ccaattgctg agtaacaaat gagacgctgt ggccaaactc     300
agtcataact aatgacattt ctagacaaag tgacttcaga ttttcaaagc gtaccctgtt     360
tacatcattt tgccaatttc gcgtactgca accggcgggc cacgcccccg tgaaaagaag     420
gttgttttct ccacatttcg gggttctgga cgtttcccgg ctgcggggcg ggggagtct     480 ccggcgcacg cggcccccttg gccccgcccc cagtcattcc cggccactcg cgacccgagg     540
ctgccgcagg gggcgggctg agcgcgtgcg aggcgattgg tttggggcca gagtgggcga     600
ggcgcggagg tctggcctat aaagtagtcg cggagacggg gtgctggttt gcgtcgtagt     660
ctcctgcagc gtctggggtt tccgttgcag tcctcggaac caggacctcg gcgtggccta     720
gcgagttatg gcgacgaagg ccgtgtgcgt gctgaagggc gacggcccag tgcagggcat     780
catcaatttc gagcagaagg caagggctgg gacggaggct tgtttgcgag gccgctccca     840
```

```
cccgctcgtc cccccgcgca cctttgctag gagcgggtcg cccgccaggc ctcggggccg      900
ccctggtcca gcgcccggtc ccggcccgtg ccgcccggtc ggtgccttcg cccccagcgg      960
tgcggtgccc aagtgctgag tcaccgggcg ggcccgggcg cggggcgtgg gaccgaggcc     1020 gccgcgggc tgggcctgcg cgtggcggga gcgcgggag ggattgccgc gggccgggga     1080 ggggcgggg cgggcgtgct gccctctgtg gtccttgggc cgccgccgcg ggtctgtcgt     1140
ggtgcctgga gcggctgtgc tcgtcccttg cttggccgtg ttctcgttcc tgagggtccc     1200
gcggacaccg agtggcgcag tgccaggccc agcccgggga tggcgactgc gcctgggccc     1260
gcctggtgtc ttcgcatccc tctccgcttt ccggcttcag cgctctaggt cagggagtct     1320
tcgcttttgt acagctctaa ggctaggaat ggttttata tttttaaaag gctttggaaa      1380
acaaaaatac gcaacagaga ccgtttgtgt gacactttgc agggaagttt gctggcctct     1440
gttctaggtc atgattgggc tgcaagggca gagaaggtag ccttgaacag aggtcctttt     1500
cctcctccta agctccggga gccagaggtt taactgaccc ttttggggat ttttgagggc     1560
agtgatctta actttgggtg cacagttagc ttatttgaag atcttactaa aaatacacca     1620
gagcccaacc tccgaccaat tacatcaaaa cctgtcctag tgcagggtga gtattgctgt     1680
tttttgaaag tttccaaaag tgattttgat gtgcacctac gattgagaac tgtcgtttga     1740
ggacagtggg tggagtttcg tatttggaaa ttagaagacc tggagtttcc attacaccga     1800
attggcactt aataactgtt gtcggagcat ttcttaagcc acattttcgt aaagtggctt     1860
taaaattgct ctgccagtag gcaggttgct aagatggtca gagacaaact tctgaacgac     1920
tcttgtaaaa tatacagaaa tattttcaga acttttatca gtaaaattac aaaacgtgtt     1980
gcaaggaagg tgcttgtgat aacactgtcc ccagaaccct agtgaagtta ccaactggtg     2040
gaaaattttc tcttgcactc ggcttaaaaa tcatgaggga atatttacta tacgaatgag     2100
attcagtctt taaggggtt tacagaaacg tgagaggaca ggaacagtta gtctgtgtaa     2160
atgtctgaaa tatatgtgag ggagataatg agtttagcct ttttctttaa taggtctcca     2220
gattttctgg aaaaggttct ttggcatttg actccatttt gctgtttcat tgtcagact     2280 tcttttttgtc cctctttact tctccccaca taattcacca gtactagtgt tttgttttc     2340 agaccaagtc tcgctctgtc gcccaggctg gagtgcagtg gcgcgatctc agctcactgc     2400
aacctccgcc tcccaggttc aagcaattct cctgcctcag cctcccgggt agctgggact     2460
acaggcgcgc gccgccacgc ctggctaatt ttttatattt tagtagagac ggcgtttcac     2520
catgttggcc aggatggtct cgatctgttg acgtcgtgat ccacccgcct cggcctccca     2580
aagtgctggg attacaggcg tgagccaccc cgcccggcca ccagtgctat tcttaagacg     2640
cctctgagga atcccttctc cctggccatt gagaatccat gcatgaaccc aggttttcca     2700
ccttccctga gcagcttgca tagttccttc ttttaagcgc ctgacttcgt tttgtttggt     2760
gcccgttgta cctgagaatg agccttggat agtggagcat tccagctttc cagatatgca     2820
gagataatac attggctatc agctacttgg cttggcctat tccgtgttta aaatcttgga     2880
ctctttgcta gttttacag atcagaattt ttcacgtatt aatccagttt tcctagcttc     2940
tcttgaagaa ttttggaga tctcttcata ctgagccttc attagcccag gacagtactg     3000
ctgtagcagt tcatatattt tttcgcttcc caggcctgtg ttattcactt aagttcatag     3060
cctggtccct gcagggttgt acccgagcac agctacttag atgtcctgaa tgtattaccg     3120
gttaaatgga ggtttcaaag aacctgctgt ttttggccct gtgctcttga taacagagtg     3180
tttgagggac aactttcaca tttgagtttt tccaaaatta aaggttgtag aagagtcaca     3240
```

```
gtatctattg tcaaaaagaa aagaatttaa aaaggcagca attgccagga tacttcattt    3300
gagcaatgat attttccagt ggaaagtcac atcttaaggg ttaatgcccc ttaactgttg    3360
gccgtatttg aaaacaaacc aagctaaaaa caagagacac tgacatgttg tatgacggtg    3420
tggtgtggat gttgtgttta ttttagtcct gagatctagt tgtaacttcc ttgatttctg    3480
tatgtagcca cggagcacca ttacctgtca ccattacctg aatggctata ctgcttgctt    3540
tcattttggt agagtggaaa ggttacctag gtttcagtgc ttgaaaagat ttcagaaagc    3600
agtagtacgt ctggttagac tagaatcagt cctctcctgg gggcagtgga atataatatt    3660
ttctgactgc taattaaaaa tacctgtgat agccgggcgt ggtggcttac gcctgtaatc    3720
ccagcacttt gggaggccga gacgggtgga tcacgaggtc agcagatgga gaccatcctg    3780
gctaacacgg tgaaacccccg tctctactaa aaatgcaaaa aaattagccg ggtgtggtgg    3840
tgggcgcctg tagtcccagc tactcaggag gctgaggcag gagaatggca tgaacctggg    3900
aggcggagct tgcagtgagc cgagatcatg tcactgcact ccagcctggg cgacagagcg    3960
agactcgtct caaaaaaaaa aagaaaaaaa cttatgatgg acacttaaaa acactcactg    4020
agtggggagt ggagagcagg ggtcccaggg tagcctgttg gacatttcca gggcgacttt    4080 ttctttttt ttttttaaag tcaagtgagt atgccatatg gaaaagggtg tgcgtggaga    4140
aaaagcaagg ggctccagag tgtaggatga gacatacacc ttttgggtta aaaaggctga    4200
ggcaggagaa tggcgtgaac ccgggaggcg gagcttgcag tgagctgaga tcatgccact    4260
gcactccagc ctgggcgaca gagcgagact cttgtctcaa aataaaaaac gtttacatgt    4320
acatgtatat tcaacatgta caaatataac ctattcaaaa gtatttacta cataaatagg    4380
tacttacatt acctatttac tgtaatagtc aaagcctatg aagtatctaa cactgatgtg    4440
taggtactca ctttgcttgc cactctatta ggtgcttttt atgttattta atcatgaagc    4500
ctggccacag ggtgcttgtg cattgagtgt gggaacaaga ttaccatctc ccttttgagg    4560
acacaggcct agagcagtta agcagcttgc tggaggttca ctggctagaa agtggtcagc    4620
ctgggatttg gacacagatt tttccactcc caagtctggc tgcttttttac ttcactgtga    4680 ggggtaaagg taaatcagct gttttctttg ttcagaaact ctctccaact ttgcactttt    4740
cttaaaggaa agtaatggac cagtgaaggt gtggggaagc attaaaggac tgactgaagg    4800
cctgcatgga ttccatgttc atgagtttgg agataataca gcaggtgggt gttgtgctgt    4860
gctggtgacc catacttgtt caccctagtt agataaacag tagagtagcc cctaaacgtt    4920
aaaacccctc aacttgtttt tgttttttgag aaagggtctt gctctgtcgc tcaggctgga    4980
gtgcagtggc gctgtgcgat catggctgac cttagccttg acctcccagg ctccattgat    5040
cctcatgcct tggcccgtag ctgggactac aggtacacac caccacgcct ggctaatttt    5100
tgtatttttt tctagaggtg gggtttcatc atgttgccca ggctggtctt gaactgctgg    5160
gctcaagtgg tctatcctcc tcgacctccc aaagtgctgg gattacatgt gtgagccact    5220
gtgcctggga aaaccctcaa cttttctttt aaaaagagg tcaactttat tgtatataag    5280
cactgtgcta aaattgcagg aactgggacc atatcctgat ttttgtaata atgccagcag    5340
agtacacaca agaaaagtaa ctgcactaga ttgtgaagac tggggtggac ctgcttctga    5400
aggtccagtg ccctttgtct taagatttgg tgtagtgtgt ctttagaaac caaaaaaga    5460 gaagaagatc aaccttaaga ttagccacaa aactgggctt tgatacctag gtgtggaaaa    5520
gaaagggaaa gagttgatgt tttgtcttac agcatcattg tagaagaggg tgttttttg    5580
```

```
tttgtttgtt ttttgagacg gagtcttact ctgtggccca ggctggagtg cagtggcgcg    5640
atctcggctc actgcaagct ccgcctcccg ggttcatgcc attctcctgc ctcagccccc    5700
tgagtagctg ggactacagg tgcccgccac cccgcctggc taattttttg tattttttagt   5760
agagacgggg tttcactgtg ttagccaaga tggtctctct cctgacctcg tgatccgcct    5820
gtctcagcct cccaaagtgc tgggattaca ggcatgagcc accgcaccca gccagaagag    5880
ggtgtttttt aaagaaggca ataggaaat aaaaacttgg gctcttaact tttgtaatga     5940
tcccaggtgt ttgagctggg ggttgagggt gggtgcctcg agcaaagggg ctgcatttat    6000
ttgcataatg ccatgtaaga gtagctctac accccaaaca caggcttctt agtgggacca    6060
aagtatgata caaactgaag atggaatgca gaggattatt ggtactttgg aatatgctta    6120
aaaaaaattt ttttaaagta tttttaaaaa atcaggcaac ccctgaacca gagtaggttc    6180
agagaaactg ccaaatttta ttttcttaat ttgggattgg aagcaagtta acagaagttt    6240
atgagttaag ttgcatttag tgatcttttg ccatatttga gtaataatct gattttttg     6300
tttatagatt tcttcttaaa ttaactttat tcatcttgct aatttagttt caaatagtga    6360
tttgtaatga tcagatttga tccatttctg taattgctga aattcccccg agttgctttt    6420
tggctttacc gcctctggtc tgggaggtga ttgctctgct gcttcctgta acttgcctgc    6480
ctttctccct gtgtgggact cctgcgggtg agagcgtggc tgaagacagc cgtgttatga    6540
aagggcctcc tgtgctgtcg aggttgtgct ctgtgaatgt catcccctgg tgcacagcag    6600
caccttctac acaggataca gttggaatgc cgcccctcg agttgtgtaa ggcagcagcc     6660
ttggcccttg cacataagat gctgttgaat attctgcctg caccaagtaa agggcacaga    6720
tagaactgct tggcatatgt tgctggggag atgagttttt tgtaaagtat actacgttct    6780
taagaatttg gatcataacc atgggatttt aataatagaa aaactgttga agatcagtct    6840
ggtcccttat ttttacagtg aagaagccaa agcccagaga agggtgttaa ctttacaagt    6900
gtcagacagt agttagaact tggtggggtt tttttttttt ttttttttgag atggagtctt    6960
gctctgttgc ccaggctgga gtgcagtggt gcgatctcag ctcactgcaa cctctgcctc    7020
ccaggttcaa gcgattctcc tgcctcagcc tactaagtag ctgggactat aggtgcgcac    7080
caccacgcct agctaatttt tgtattttt cagtagagac agggtttgc tatgctggcc     7140
aggctggtct caaactcctg acctcagatg atccagccac ctcagcttcc caaagtgctg    7200
gggttccagg tgttagccac catgcctggc catagacttg tttctgttcc cttctcactg    7260
tggctgtacc aaggtgttgc ttatcccaga agtcgtgatg caggtcagca ctttctccat    7320
gggaagtttt agcagtgttt cttttttagaa tgtatttggg aactttaatt cataatttag   7380
cttttttttc ttcttcttat aaataggctg taccagtgca ggtcctcact ttaatcctct    7440
atccagaaaa cacggtgggc caaaggatga agagaggtaa caagatgctt aactcttgta    7500
ataatggcga tagcttttctg gagttcatat ggtatactac ttgtaaatat gtgctaagat    7560
aattccgtgt tccccccacc tttgcttttg aacttgctga ctcatctaaa cccctgctcc    7620
caaatgctgg aatgctttta cttcctgggc ttaaaggaat tgacaaatgg ggacacttaa    7680
aacgatttgg ttttgtagca tttattgaat atagaactaa tacaagtgcc aaggggaac     7740
taatacagga aatgtcatga acagtactgt caaccactag caaaatcaat catcattgtg    7800
aaacatagga agcttctgta gataaaaaaa aaaattgata ctgaaaacta gtcgagactc    7860
catttatatg tgtatgtttt ctgaaagcct ttcagaaaaa tattaaattt aaggacaaga    7920
ttttttatatc agaggccttg ggacatagct ttgttagcta tgccagtaat taacaggcat   7980
```

```
aactcagtaa ctgagagttt acccttggt acttctgaaa tcaggtgcag ccccatcttt    8040
cttcccagag cattagtgtg tagacgtgaa gccttgtttg aagagctgta tttagaatgc    8100
ctagctactt gtttgcaaat tgtgtctac tcagtcaagt tttaatttag ctcatgaact    8160
accttgatgt ttagtggcat cagccctaat ccatctgatg cttttcatt attaggcatg    8220 ttggagactt gggcaatgtg actgctgaca aagatggtgt ggccgatgtg tctattgaag    8280
attctgtgat ctcactctca ggagaccatt gcatcattgg ccgcacactg gtggtaagtt    8340
ttcataaaag gatatgcata aaacttcttc taacatacag tcatgtatct tttcactttg    8400
attgttagtc gcggtttcta aagatccaga taaactgtac ttgcagttca aattaggaaa    8460
agcaatttta ttggacaatt acggtgaaaa tgaattattt tatctaggtc agttaagaac    8520
actgttctgc taagatgcag taaaaagcag gttacatttg accatattag atctgagttt    8580
ggaaaacaga agtagtcttt agttttaaaa tggccagatt ttcttgccag gattgggttt    8640
ctcacttgtt aaacagaaca ttttgttaag tttaaaacct gggatggact taagtattca    8700
tgttcattca tgttcattca ggactgcagg ttatcatgac ttgtttaact tgtgggaagc    8760
tgttgtccca agttatcctg gggaactgca tctggttctt gcaaacacc aagtagacag    8820 gctctctttt acctcccctt gagggcatta acattcagta gtcacttcca ttcagttaac    8880
cctttatttt tatggttttt cttgagccat agttgtaaag cagaaaaatc atttataaag    8940
gtttgttgaa caaaattcaa aatactgttg cttaaagtat taagatttt taggattata    9000 ccttacttat aggcccgtca ttcatttggc atgaaatttt gagtttatt cactttcact    9060 ttcctttttt tccaaagcaa ttaaaaaaac tgccaaagta agagtgactg cggaactaag    9120
gttactgtaa cttaccatgg aggattaagg gtagcgtgtg gtggtctaca acatagttat    9180
ttgggtttta gtatttcatt tagacagcaa cacttaccta atgttaaaag gtaatgtctt    9240
tgcaacacca agaaaaagct ttgagtagta gtttctactt ttaaactact aaatattagt    9300
atatctctct actaggatta atgttatttt tctaatatta tgaggttctt aaacatcttt    9360
tgggtattgt tgggaggagg tagtgattac ttgacagccc aaagtatct tcttaaaatt    9420 ttttacaggt ccatgaaaaa gcagatgact tgggcaaagg tggaaatgaa gaaagtacaa    9480
agacaggaaa cgctggaagt cgtttggctt gtggtgtaat tgggatcgcc caataaacat    9540
tcccttggat gtagtctgag gcccttaac tcatctgtta tcctgctagc tgtagaaatg    9600
tatcctgata aacattaaac actgtaatct aaaagtgta attgtgtgac ttttcagag    9660 ttgctttaaa gtacctgtag tgagaaactg atttatgatc acttggaaga tttgtatagt    9720
tttataaaac tcagttaaaa tgtctgtttc aatgacctgt attttgccag acttaaatca    9780
cagatgggta ttaaacttgt cagaatttct ttgtcattca agcctgtgaa taaaaaccct    9840
gtatggcact tattatgagg ctattaaaag aatccaaatt caaactaaat tagctctgat    9900
acttatttat ataaacagct tcagtggaac agattagta atactaacag tgatagcatt    9960
ttattttgaa agtgttttga gaccatcaaa atgcatactt taaaacagca ggtcttttag   10020
ctaaaactaa cacaactctg cttagacaaa taggctgtcc tttgaaagct ttagggaaat   10080
gttcctgctt agtcatttta gcattttgat tcataagta cctcctcatt ttaaaaagac   10140
attatgatgt aagagagcca tttgataact ttttagtgag ctttgaaagg caagttacag   10200
cctcagctag ctagtaagat tatctacctg ccagaatggc acaaattcta cattcaaggg   10260
tagacgctgg cacaacctac ttacagatta gcccttaaa gcaatctgta gcattagaag   10320
```

| | |
|---|---|
| atggaaccaa ggaaatgttt gactgtgggt tctggctgtt gagaaataat ttacacaccg | 10380 |
| aattagtgaa atgagtcact ttctcttaat gtatttatgt acctgagaga atgcttttca | 10440 |
| atgttaacct aactcaggtt tgactaaatt attcaattgg aaattgtaga atattatttc | 10500 |
| tgataaacca gaaataagtg aaatgctgtt tgttcataaa tatgtacttt atcaaatgta | 10560 |
| ggagagatca tttaggagag gaaaagctaa attggaagac aaatctgtag tgtttccaaa | 10620 |
| gttttaaaat tatggtaaac aacagtatgt tcacagtaag tggttaaaac aaccattctt | 10680 |
| taaatctcag tagagaattt ttaaaaagca gtatttaaca catttcccta atgtagtttg | 10740 |
| ttgcctatgt ggataactc aattagagac tcacttatgc cttttgaaac ttcaaatata | 10800 |
| attacactac cagttttttac atgtgcatat aggatggtcc caatacttta aattggaaat | 10860 |
| acaggctgta agtccttcaa gtctggatgt tgggtaatca cgttttcttc cagaagccat | 10920 |
| ttgttaggac tttaaaactt ctcagtgggc cagtgtaaaa ttaaggacaa gttttataat | 10980 |
| ttaaatttac agataaatat | 11000 |

<210> SEQ ID NO 11
<211> LENGTH: 438
<212> TYPE: DNA
<213> ORGANISM: Homo sapiens
<220> FEATURE:

<400> SEQUENCE: 11

| | |
|---|---|
| cgacggccca gtgcagggca tcatcaattt cgagcagaag gctgtaccag tgcaggtcct | 60 |
| cactttaatc ctctatccag aaaacacggt gggccaaagg atgaagagag gcatgttgga | 120 |
| gacttgggca atgtgactgc tgacaaagat ggtgtggccg atgtgtctat tgaagattct | 180 |
| gtgatctcac tctcaggaga ccattgcatc attggccgca cactggtggt ccatgaaaaa | 240 |
| gcagatgact tgggcaaagg tggaaatgaa gaaagtacaa agacaggaaa cgctggaagt | 300 |
| cgtttggctt gtggtgtaat tgggatcgcc caataaacat tcccttggat gtagtctgag | 360 |
| gccccttaac tcatctgtta tcctgctagc tgtagaaatg tatcctgata aacattaaac | 420 |
| actgtaatct taaaaaaa | 438 |

<210> SEQ ID NO 12
<211> LENGTH: 499
<212> TYPE: DNA
<213> ORGANISM: Homo sapiens
<220> FEATURE:
<221> NAME/KEY: misc_feature
<222> LOCATION: 462, 499
<223> OTHER INFORMATION: n = a, t, c, or g

<400> SEQUENCE: 12

| | |
|---|---|
| tttggggcca gagtgggcga ggcgcggagg tctggcctat aaagtagtcg cggagacggg | 60 |
| gtgctggttt gcgtcgtagt ctcctgcagc gtctggggtt tccgttgcag tcctcggaac | 120 |
| caggacctcg gcgtggccta gcgagttatg gcgacgaagg ccgtgtgcgt gctgaagggc | 180 |
| gacggccagt tgcagggcat catcaatttc gagcagaagg aaagtaatgg accagtgaag | 240 |
| gtgtggggaa gcattaaagg actgactgaa ggcctgcatg gattccatgt tcatgagttt | 300 |
| ggagataata cagcaggctg taccagtgca ggtcctcact ttaatcctct atccagaaaa | 360 |
| cacggtgggc caaaggatga agagaggcat gttggagact gggcaatgt gactgctgac | 420 |
| aaagatggtg tggccgatgt gtctattgaa gattctgtga tnctccactc tccaggagac | 480 |
| cattgcatca ttggccgtn | 499 |

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
tcagcacgca cacggccttc                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
gcccttcagc acgcacacgg                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gtcgcccttc agcacgcaca                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
cgaggactgc aacggaaacc                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ggttccgagg actgcaacgg                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tcctggttcc gaggactgca                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gaggtcctgg ttccgaggac                                                    20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
taggccacgc cgaggtcctg                                                    20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
gtcgccataa ctcgctaggc                                                    20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gccctgcact gggccgtcgc                                                    20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
aattgatgat gccctgcact                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cactggtcca ttactttcct                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
acaccttcac tggtccatta                                                    20

<210> SEQ ID NO 26

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ccacaccttc actggtccat                                                   20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
agtcctttaa tgcttcccca                                                   20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
aggccttcag tcagtccttt                                                   20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
caggccttca gtcagtcctt                                                   20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tatctccaaa ctcatgaaca                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gctgtattat ctccaaactc                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
```
gtacagcctg ctgtattatc                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tgcccaagtc tccaacatgc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cacattgccc aagtctccaa                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tcggccacac catctttgtc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
catcggccac accatctttg                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
acacatcggc cacaccatct                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tagacacatc ggccacacca                                              20

<210> SEQ ID NO 39
<211> LENGTH: 20
<212> TYPE: DNA

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
accaccagtg tgcggccaat                                                 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
catggaccac cagtgtgcgg                                                 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tcatggacca ccagtgtgcg                                                 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ggcgatccca attacaccac                                                 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ggaatgttta ttgggcgatc                                                 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cctcagacta catccaaggg                                                 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gataacagat gagttaaggg                                                 20

```
<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cacaattaca cttttaagat                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
agtcacacaa ttacactttt                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ctcactacag gtactttaaa                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
aatcagtttc tcactacagg                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ataaatcagt ttctcactac                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cataaatcag tttctcacta                                               20

<210> SEQ ID NO 52
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 52
aatcttccaa gtgatcataa                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
atacaaatct tccaagtgat                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tgagttttat aaaactatac                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
aactgagttt tataaaacta                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
acagacattt taactgagtt                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
attgaaacag acattttaac                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tcattgaaac agacattta                                                     20

```
<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
atacaggtca ttgaaacaga                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ccatctgtga tttaagtctg                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tttaataccc atctgtgatt                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
agtttaatac ccatctgtga                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
caaagaaatt ctgacaagtt                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ttgaatgaca aagaaattct                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 65
acaggcttga atgacaaaga                                           20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
attcacaggc ttgaatgaca                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ggtttttatt cacaggcttg                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
agggttttta ttcacaggct                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
atacagggtt tttattcaca                                           20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ccatacaggg ttttattca                                            20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
aagtgccata cagggttttt                                           20

<210> SEQ ID NO 72
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 72
taataagtgc catacagggt                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tcataataag tgccatacag                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ctcataataa gtgccataca                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gcctcataat aagtgccata                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ttttaatagc ctcataataa                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ggattctttt aatagcctca                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
```

| | |
|---|---|
| cagcccttgc cttctgctcg | 20 |

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79

| | |
|---|---|
| agtagctggg actacaggcg | 20 |

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80

| | |
|---|---|
| cattactttc ctttaagaaa | 20 |

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81

| | |
|---|---|
| aagatcacta aatgcaactt | 20 |

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82

| | |
|---|---|
| caggagaatc gcttgaacct | 20 |

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

| | |
|---|---|
| ctggtacagc ctatttataa | 20 |

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

| | |
|---|---|
| gcttcacgtc tacacactaa | 20 |

<210> SEQ ID NO 85
<211> LENGTH: 20
<212> TYPE: DNA
<213> ORGANISM: Artificial Sequence

```
-continued

<220> FEATURE:
<223> OTHER INFORMATION: Antisense Oligonucleotide

<400> SEQUENCE: 85
tccaacatgc ctaataatga                                                  20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tggtacagcc ttctgctcga                                                  20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
taggccagac ctccgcgcct                                                  20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
actttatagg ccagacctcc                                                  20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gacgcaaacc agcaccccgt                                                  20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
acgctgcagg agactacgac                                                  20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gcacacggcc ttcgtcgcca                                                  20
```

```
<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ttcagcacgc acacggcctt                                                    20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
ccttcagcac gcacacggcc                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
cccttcagca cgcacacggc                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cgcccttcag cacgcacacg                                                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tcgcccttca gcacgcacac                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
cgtcgccctt cagcacgcac                                                    20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 98
ccgtcgccct tcagcacgca                                          20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
caacatgcct ctcttcatcc                                          20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ccaacatgcc tctcttcatc                                          20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
tccaacatgc ctctcttcat                                          20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
ctccaacatg cctctcttca                                          20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
tctccaacat gcctctcttc                                          20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gtctccaaca tgcctctctt                                          20

<210> SEQ ID NO 105

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ctcctgagag tgagatcaca                                                   20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tctcctgaga gtgagatcac                                                   20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
cacctttgcc caagtcatct                                                   20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
ccacctttgc ccaagtcatc                                                   20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
tccacctttg cccaagtcat                                                   20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
ttccaccttt gcccaagtca                                                   20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
```
atttccacct ttgcccaagt 20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
catttccacc tttgcccaag 20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
tcatttccac ctttgcccaa 20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
ttcatttcca cctttgccca 20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
cttcatttcc acctttgccc 20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
tcttcatttc cacctttgcc 20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
ttcttcattt ccacctttgc 20

<210> SEQ ID NO 118
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 118
tttcttcatt tccacctttg                                                    20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
ctttcttcat ttccaccttt                                                    20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
actttcttca tttccacctt                                                    20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
tactttcttc atttccacct                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
gtactttctt catttccacc                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tgtactttct tcatttccac                                                    20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
ttgtactttc ttcatttcca                                                    20

```
<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tttgtacttt cttcatttcc                                               20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
ctttgtactt tcttcatttc                                               20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
tctttgtact ttcttcattt                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
gtctttgtac tttcttcatt                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
cattactttc cttctgctcg                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tccaacatgc ctctcttcat                                               20

<210> SEQ ID NO 131
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 131
cattactttc ctttaagaaa                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
caacacccac ctgctgtatt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
ctggtacagc ctatttataa                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
catcttgtta cctctcttca                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tccaacatgc ctaataatga                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
gaaaacttac caccagtgtg                                               20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ttttcatgga cctgtaaaaa                                               20

```
<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ggattctttt aatagcctca                                              20

<210> SEQ ID NO 139
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 139
tactttcctt ctgct                                                   15

<210> SEQ ID NO 140
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 140
aacatgcctc tcttc                                                   15

<210> SEQ ID NO 141
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 141
tactttcctt taaga                                                   15

<210> SEQ ID NO 142
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 142
cacccacctg ctgta                                                   15

<210> SEQ ID NO 143
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 143
gtacagccta tttat                                                   15

<210> SEQ ID NO 144
<211> LENGTH: 15
<212> TYPE: DNA
<213> ORGANISM: Artificial Sequence
<220> FEATURE:
<223> OTHER INFORMATION: Antisense Oligonucleotide
```

```
<400> SEQUENCE: 144
cttgttacct ctctt                                                    15

<210> SEQ ID NO 145
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 145
aacatgccta ataat                                                    15

<210> SEQ ID NO 146
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 146
aacttaccac cagtg                                                    15

<210> SEQ ID NO 147
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 147
tcatggacct gtaaa                                                    15

<210> SEQ ID NO 148
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 148
ttcttttaat agcct                                                    15

<210> SEQ ID NO 149
<211> LENGTH: 650
<212> TYPE: DNA
<213> ORGANISM: R. norvegicus
<220> FEATURE:
<221> NAME/KEY: CDS
<222> LOCATION: (94)...(558)

<400> SEQUENCE: 149
gttttgcacc ttcgtttcct gcggcggctt ctgtcgtctc cttgcttttt gctctcccag   60
gttccgaggc cgccgcgcgt ctcccgggga agc atg gcg atg aag gcc gtg tgc  114
                                    Met Ala Met Lys Ala Val Cys
                                     1               5 gtg ctg aag ggc gac ggt ccg gtg cag ggc gtc att cac ttc gag cag   162
Val Leu Lys Gly Asp Gly Pro Val Gln Gly Val Ile His Phe Glu Gln
            10                  15                  20 aag gca agc ggt gaa cca gtt gtg gtg tca gga cag att aca gga tta   210
Lys Ala Ser Gly Glu Pro Val Val Val Ser Gly Gln Ile Thr Gly Leu
        25                  30                  35 act gaa ggc gag cat ggg ttc cat gtc cat caa tat ggg gac aat aca   258
Thr Glu Gly Glu His Gly Phe His Val His Gln Tyr Gly Asp Asn Thr
```

```
                   40                   45                   50                   55
caa ggc tgt acc act gca gga cct cat ttt aat cct cac tct aag aaa     306
Gln Gly Cys Thr Thr Ala Gly Pro His Phe Asn Pro His Ser Lys Lys
                60                   65                   70 cat ggc ggt cca gcg gat gaa gag agg cat gtt gga gac ctg ggc aat     354
His Gly Gly Pro Ala Asp Glu Glu Arg His Val Gly Asp Leu Gly Asn
            75                   80                   85 gtg gct gct gga aag gac ggt gtg gcc aat gtg tcc att gaa gat cgt     402
Val Ala Ala Gly Lys Asp Gly Val Ala Asn Val Ser Ile Glu Asp Arg
        90                   95                  100 gtg atc tca ctc tca gga gag cat tcc atc att ggc cgt act atg gtg     450
Val Ile Ser Leu Ser Gly Glu His Ser Ile Ile Gly Arg Thr Met Val
    105                  110                  115 gtc cac gag aaa caa gat gac ttg ggc aaa ggt gga aat gaa gaa agt     498
Val His Glu Lys Gln Asp Asp Leu Gly Lys Gly Gly Asn Glu Glu Ser
120                  125                  130                  135 aca aag act gga aat gct gga agc cgc ttg gct tgt ggt gtg att ggg     546
Thr Lys Thr Gly Asn Ala Gly Ser Arg Leu Ala Cys Gly Val Ile Gly
                140                  145                  150 att gcc caa taa acattccctc tgtggtctga gtctcagact catctgctgt         598
Ile Ala Gln  * cctgctaaac tgtagaaaaa aaccaaacca ttaaactgta atcttaacag tt           650

<210> SEQ ID NO 150
<211> LENGTH: 2026
<212> TYPE: DNA
<213> ORGANISM: R. norvegicus

<400> SEQUENCE: 150
ggatccgatg ccctcttctg gtgtgtctga agacatattt aaaagaaaag aaagaaataa     60
gactctccag gatagtcata gagcagagcc caggggtcta cataagtaac tgtatcccag    120
tgtagccaat cagttcctcc tgtttctctg gcctagagtt aggtttcggt attttgccat    180
cctcagaatt aaatcctgcc tcctgagtgt agcagaacat gcagttttat gcatgagctc    240
ttgggagacc acagagattt caattttaaa aagagacagt tttcttttt agttgagaaa     300 acaactttaa cggtccccag ctccggaaaa aaaaaaaa aagaaagaaa caactttaaa      360
aagagacaat tctgttttta gttaagaatt ctctctctta ctgataccct ttcttggctc    420
cagggactcc ccatatatct ttctagacat ttctgagaac tcaagtaaat atatggtgat    480
gtctccccac ctttttttgt agtttgtacc ttttgctcat tccataccgt cttagaaaat    540
atcttccttg aagcactatg tctcacccag tgcatggagt ttcacaaatg acttcatcag    600
gcatcttgtt ctccagcgca ggctgtctga gaacacttca acaggcaaag aggatacgaa    660
tgttactatg aagtaacacg actggggatg gtgggcagac gactaatcgt atactgatat    720
gggtactgag acgagggta ctgagacgga ggatctcaaa tgaagtttag tcccatctct     780
aaagttaaaa gaaagccagg tacacgcctc taaccccagc aactgggagg cagaggtcag    840
aggcagggag agccctgtga gtttgaggtc gctggtctgc ataatgagtt ctgtgatagc    900
caaggtatac acggtgtgat atttttaaaa ggaggtgtgt caaccggcag agcacatgtc    960
tgtcacgagg ggtgtgtgta gtcaaatccc cagtaccaag taacaaaaac attagtgaag   1020
aataagtaac gtgatatgtg cccaggaatt agaaacctgc agagagggt tggggattta    1080 gctcagtggt agacggcttg cctaggaagc gcaaggccct gggttcgatt ccccagctcc   1140
gaaaaaaaga accccccccc caaaaaaaag aaacctgcag agaaaaaaaa aaaacctgca   1200
```

```
gagacacaga ggtgtgtctg gagatagaac atgggcctta cacatattac accgagcatc   1260
catcttggct caccccaact ttcacacagc aactgcggcg cgctgcaaag tcagtcgcaa   1320
tccgcatttc tagacagagc ggcttcagac cttccaggcg cgcacgcagg cctcgccgag   1380
gtttcctccg cgactcggcc gacttcacag ttagaagaca atagcgactt tcccagctct   1440
gtctcgattc tggaactttc tcagtcgcaa gctcctgaag ctggcgctcc cctcagcccc   1500
gcccccaacg tgcccgcgg ccagggaact tcaggaaggg taggcagaga ccgcggctag    1560
cgattggttc cctgccaagg tgggagtggc caggcacagg catataaaag ctccgcggcg   1620
ctgggccctc gttttgcacc ttcgtttcct gcggcggctt ctgtcgtctc cttgcttttt   1680
gctctcccag gttccgaggc cgccgcgcgt ctcccgggga agcatgatgg cgacgatggc   1740
cgtgtgcgtc ctgaagggcg acggtccggt gcagggcgtc attcacttcg agcagaaggc   1800
aaggcccggg gcgctggagc cagagccagc ggtgacggcg acacctagt gcgggacgca    1860 gccacgcccc cgccgcggcc tgagcccgtt aaatgctgag tcaccgcggc cttgaggagg   1920
ggcggcgcgg actagggagg cggggcgccg cggggacctt cggcgggtct ctcgcgcccc   1980
gagtgcgggc gccgagagag cagtttgcat cgctatccta tggact                 2026

<210> SEQ ID NO 151
<211> LENGTH: 550
<212> TYPE: DNA
<213> ORGANISM: R. norvegicus

<400> SEQUENCE: 151
ggatccccac aggcagtagg acacaattat tttctggcta ctggataaat tatgggaact     60
gataaacatc actgaatgtg gagtagaggt ttctgggcag ccaatgttct gaagagtcaa    120
gcctgacaca gtgcagtagc catccattcc ctagttctga cattgagctg ccccctttg     180 ttcctctggg tgcttttcaa gtgctgttga gtccaggtgt ctgcacacgt gcatctggaa    240
acaagtgtta gggccgatgg gtagggaggg agaggcctag agctaagcag ctctagagtc    300
accctggagg aaatgggtct acttggattt ggacataggt ttgattttgt tttgtttttt    360
gcattgtgcc ttttcatgt gattcagagt attacacaaa cttgatgtct tattttgta     420 ttttttaaat aaggcaagcg gtgaaccagt tgtggtgtca ggacagatta caggattaac    480
tgaaggcgag catgggttcc atgtccatca atatgggac aatacacaag gtaggtccta     540
ggctggctag                                                           550

<210> SEQ ID NO 152
<211> LENGTH: 338
<212> TYPE: DNA
<213> ORGANISM: R. norvegicus

<400> SEQUENCE: 152
ctctagagtc accctggagg aaatgggtct acttggattt ggacataggt ttgttttgat     60
tttgtttttt gacttgtgcc ttttactgtg attcagaagt attaacacaa acttgatgtc    120 ttaattttg tattttttta aataaaggca agcggtgaac cagttgtggt gtcaggacag    180
attacaggat taactgaagg cgagcatggg ttccatgtcc atcaatatgg ggacaataca    240
caaggtaagt cttaatctat ctctacctgg tctgactagt gagatgaatg ggtcagagtc    300
aggaccaatt actaaccatt taaaaccatc aattttttt                          338

<210> SEQ ID NO 153
<211> LENGTH: 799
```

```
<212> TYPE: DNA
<213> ORGANISM: R. norvegicus

<400> SEQUENCE: 153
ctgcagatat catgggctgt ggtagtgaga ccctgtctca aatctcaaaa caaacaaaca      60
tgacagtcta gtgaaaaagc gggtagcttg aaaattgcaa ggccatatag tccagcctat     120
ttgtaccagg gtgctgcttc ctgtttgtat cactccagca cataccagct ccatgtttgc     180
tgtgttggaa gttgtaagaa ttccgatgtc attgcataca gaggtttact tcataatctg     240
actgctggtt tctggtaata ggctgtacca ctgcaggacc tcattttaat cctcactcta     300
agaaacatgg cggtccagcg gatgaagaga ggtgagcagc attctctcat gcatggtggt     360
ggagaggggc tgtggaaaa cacctgaaga cagaactgag tggtctcact gccttttctt      420
ttgtatgttt ccattcaccc aactcccaca tccccaagta ctggaatagt ttatattggg     480
tgaaggagct gacaaatgtg gactcttaag tgatttagtt ttgtagcatt tattgaagat     540
gaactaatac aagtgccaaa aggaaccaat acagaaaata tcatggataa cagtactatc     600
acgtcactag caaaggtaaa tcattgtata atatcattaa tgcagattaa taaaaactag     660
ttgagattcc gtttgtatgt gaaccttagg aagtccttca tattaagagg ctagctcttt     720
gaatgagctg gagcaaacct tcgtaatcag gagctgcata cttcgtaacc tcgaagtgcc     780
ttcttctaga gcagagtga                                                  799

<210> SEQ ID NO 154
<211> LENGTH: 476
<212> TYPE: DNA
<213> ORGANISM: R. norvegicus

<400> SEQUENCE: 154
attagacatt agatccctat gattgggaaa taggcatgtt ggagacctgg gcaatgtggc      60
tgctggaaag gacggtgtgg ccaatgtgtc cattgaagat cgtgtgatct cactctcagg     120
agagcattcc atcattggcc gtactatggt ggtaagtttc catatagtag tagatgtagg     180
atttcttcta acatagttat gtacctttcc atgacttcgt ggtggtggtt aaactagttc     240
ctaaaagatc acataaattg gtaagatgtt cagaatagga aaaaatatta ttttattgga     300
tgtaatagta aagaattaat ttgcctagtc agttaagaac gctcgttctg ctcgaagtgc     360
tggtagaaag ctggttacat ttgatcagac tggatctgag ttgaggatac aatagtcttt     420
agtttaaaac agctggattt tcttgccatg attgccccct tacagttaat catttc         476

<210> SEQ ID NO 155
<211> LENGTH: 630
<212> TYPE: DNA
<213> ORGANISM: R. norvegicus

<400> SEQUENCE: 155
cttagtagtc tgacttttag ctgatggcaa aaaattagct tattgattta ctaatagatt      60
tgaacatttt ctaatataca tggtccttg aagtattgct gggaagaagt gctaattact      120
tacttgatca cagaaaccta atgttctta attcttttca aaggtccacg agaaacaaga      180
tgacttgggc aaaggtggaa atgaagaaag tacaaagact ggaaatgctg gaagccgctt     240
ggcttgtggt gtgattggga ttgcccaata acattccct atgtggtctg agtctcagac      300
tcatctgctg tcctgctaaa ctgtagaaac caaaccatta aactgtaatc ttaacagttg     360
ttccaatgtg tgtgcatccc tttgcttact gctaaggcat ccgtgagtga gaggtgctac     420
```

```
gagtaggttt ggaggtatgt ggttgacaat tcctgaatgt gtacaactct tagaactaaa      480
tagtgttgtt ttctgtgccc agaccctcac tgggtggttt aagctgaaat ttctctttca      540
agcctctctc tctctctgtg tgtgtgtctg tgtgtgtgtg tgtgtgtgtg tgtgtgtgtg      600
agagagagag actgagactt atttagagct                                        630

<210> SEQ ID NO 156
<211> LENGTH: 544
<212> TYPE: DNA
<213> ORGANISM: R. norvegicus

<400> SEQUENCE: 156
ttagtattca tctagaaata gccacgagca aggaaacact tagtagtctg cttttagctg       60
atagcataaa aattagctta ttgatttact aatagatttg aacattttct aatatacatg      120
gtcctttgaa gtattgctgg gaagaagtgc taattacttg atcaccgaaa cctaaatgtt      180
cttaattctt ttcaaaggtc cacgagaaac aagatgactt gggcaaaggt ggaaatgaag      240
aaagtacaaa gactggaaat gctggaagcc gcttggcttg tggtgtgatt gggattgccc      300
aataaacatt ccctatgtgg tctgagtctc agactcatct gctgtcctgc taaactgtag      360
aaaaaaacca aaccattaaa ctgtaatctt aacagttgtt aactgtgtga ctcctttgac      420
ttgctctaag gacttgcagt gagaggtgac tgacgatgtt tggaggatgt gtagaacttc      480
ctgaatgtgt acaactcatt gaactaaaat ctgttgtttc tgtgccagac ctcactggtg      540
taag                                                                   544

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
gtgcgcgcga gcccgaaatc                                                   20

<210> SEQ ID NO 158
<220> FEATURE:

<400> SEQUENCE: 158

000

<210> SEQ ID NO 159
<211> LENGTH: 16
<212> TYPE: DNA
<213> ORGANISM: Artificial Sequence
<220> FEATURE:
<223> OTHER INFORMATION: PCR Primer

<400> SEQUENCE: 159
tgctgaaggg cgacgg                                                       16

<210> SEQ ID NO 160
<211> LENGTH: 19
<212> TYPE: DNA
<213> ORGANISM: Artificial Sequence
<220> FEATURE:
<223> OTHER INFORMATION: PCR Primer

<400> SEQUENCE: 160
gttcaccgct tgccttctg                                                    19
```

```
<210> SEQ ID NO 161
<211> LENGTH: 23
<212> TYPE: DNA
<213> ORGANISM: Artificial Sequence
<220> FEATURE:
<223> OTHER INFORMATION: PCR Probe

<400> SEQUENCE: 161
ccggtgcagg gcgtcattca ctt                                          23

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
cgcaggaaac gaaggtgcaa                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
gccgcaggaa acgaaggtgc                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
ctcggaacct gggagagcaa                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
ttcatcgcca tgcttccccg                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
acggccttca tcgccatgct                                              20

<210> SEQ ID NO 167
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 167
cacacggcct tcatcgccat                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
tcagcacgca cacggccttc                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
gcccttcagc acgcacacgg                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
gtcgcccttc agcacgcaca                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
ggaccgtcgc ccttcagcac                                              20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
ctgctcgaag tgaatgacgc                                              20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
cttgccttct gctcgaagtg                                              20

```
<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
caccgcttgc cttctgctcg                                               20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
tggttcaccg cttgccttct                                               20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
acaactggtt caccgcttgc                                               20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
taatctgtcc tgacaccaca                                               20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
tcctgtaatc tgtcctgaca                                               20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
ttaatcctgt aatctgtcct                                               20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 180
ccatgctcgc cttcagttaa                                         20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
acatggaacc catgctcgcc                                         20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
attgatggac atggaaccca                                         20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
ccttgtgtat tgtccccata                                         20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
tacagccttg tgtattgtcc                                         20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
gtgaggatta aaatgaggtc                                         20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
cttagagtga ggattaaaat                                         20

<210> SEQ ID NO 187
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 187
tgtttcttag agtgaggatt                                               20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
ttgcccaggt ctccaacatg                                               20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
acattgccca ggtctccaac                                               20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
cacaccgtcc tttccagcag                                               20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
ttggccacac cgtcctttcc                                               20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
acattggcca caccgtcctt                                               20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
```

-continued acacattggc cacaccgtcc                                                      20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
aatggacaca ttggccacac                                                      20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
tcttcaatgg acacattggc                                                      20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
cacgatcttc aatggacaca                                                      20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
tcacacgatc ttcaatggac                                                      20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
gatcacacga tcttcaatgg                                                      20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
cggccaatga tggaatgctc                                                      20

<210> SEQ ID NO 200
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 200
tagtacggcc aatgatggaa                                               20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
tcgtggacca ccatagtacg                                               20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
ttctcgtgga ccaccatagt                                               20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
cggcttccag catttccagt                                               20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
ccaagcggct tccagcattt                                               20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
cacaagccaa gcggcttcca                                               20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
tcacaccaca agccaagcgg                                               20
```

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
gcaatcccaa tcacaccaca                                                  20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
tgggcaatcc caatcacacc                                                  20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
ttattgggca atcccaatca                                                  20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
cacataggga atgtttattg                                                  20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
tcagaccaca tagggaatgt                                                  20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
agactcagac cacataggga                                                  20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 213
tctgagactc agaccacata                                                     20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
caggacagca gatgagtctg                                                     20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
tagcaggaca gcagatgagt                                                     20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
acagtttagc aggacagcag                                                     20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
tctacagttt agcaggacag                                                     20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
gattacagtt taatggtttg                                                     20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
tagcgatgca aactgctctc                                                     20

<210> SEQ ID NO 220
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
ataggatagc gatgcaaact                                              20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
taggacctac cttgtgtatt                                              20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
taagacttac cttgtgtatt                                              20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
actctgaccc attcatctca                                              20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
gctgctcacc tctcttcatc                                              20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
ttgctagtga cgtgatagta                                              20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
```

```
atacaaacgg aatctcaact                                              20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
ctccagctca ttcaaagagc                                              20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
agtatgcagc tcctgattac                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
gaaggcactt cgaggttacg                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
ggaaacttac caccatagta                                              20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
tatggaaact taccaccata                                              20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
gcaaattaat tctttactat                                              20

<210> SEQ ID NO 233
<211> LENGTH: 20
<212> TYPE: DNA
```

-continued

```
<213> ORGANISM: Artificial Sequence
<220> FEATURE:
<223> OTHER INFORMATION: Antisense Oligonucleotide

<400> SEQUENCE: 233
gtatcctcaa ctcagatcca                                              20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
tctcgtggac ctttgaaaag                                              20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
agcagactac taagtgtttc                                              20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
ttttatgcta tcagctaaaa                                              20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
taaatcaata agctaatttt                                              20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
gttcaaatct attagtaaat                                              20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
ctcgtggacc tttgaaaaga                                              20
```

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
tgggagagca aaaagcaagg                    20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
gaacctggga gagcaaaaag                    20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
gcctcggaac ctgggagagc                    20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
cggcctcgga acctgggaga                    20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
ggcggcctcg gaacctggga                    20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
catgcttccc cgggagacgc                    20

<210> SEQ ID NO 246
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 246
tcgccatgct tccccgggag                                               20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
catcgccatg cttccccggg                                               20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
gccttcatcg ccatgcttcc                                               20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
gcacgcacac ggccttcatc                                               20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
cttcagcacg cacacggcct                                               20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
ttctgctcga agtgaatgac                                               20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
tgccttctgc tcgaagtgaa                                               20
```

```
<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
cgcttgcctt ctgctcgaag                                               20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
ttcaccgctt gccttctgct                                               20

<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
ccacaactgg ttcaccgctt                                               20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
caccacaact ggttcaccgc                                               20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
tgtcctgaca ccacaactgg                                               20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
tctgtcctga caccacaact                                               20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 259
tgtaatctgt cctgacacca                                               20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260
aatcctgtaa tctgtcctga                                               20

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
agttaatcct gtaatctgtc                                               20

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 262
tcagttaatc ctgtaatctg                                               20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
acccatgctc gccttcagtt                                               20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
atggaaccca tgctcgcctt                                               20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
ggacatggaa cccatgctcg                                               20

<210> SEQ ID NO 266
<211> LENGTH: 20
```

<212> TYPE: DNA
<213> ORGANISM: Artificial Sequence
<220> FEATURE:
<223> OTHER INFORMATION: Antisense Oligonucleotide

<400> SEQUENCE: 266
tgatggacat ggaacccatg                                          20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
catattgatg gacatggaac                                          20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 268
cccatattga tggacatgga                                          20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
tccccatatt gatggacatg                                          20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
tgtccccata ttgatggaca                                          20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
attgtcccca tattgatgga                                          20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272

| tgtgtattgt ccccatattg | 20 |

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273

| agccttgtgt attgtcccca | 20 |

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274

| ttcttagagt gaggattaaa | 20 |

<210> SEQ ID NO 275
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 275

| catgtttctt agagtgagga | 20 |

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276

| gccatgtttc ttagagtgag | 20 |

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277

| gaccgccatg tttcttagag | 20 |

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278

| tggaccgcca tgtttcttag | 20 |

<210> SEQ ID NO 279
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 279
gctggaccgc catgtttctt                                              20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
ccgctggacc gccatgtttc                                              20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281
atccgctgga ccgccatgtt                                              20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282
tcatccgctg gaccgccatg                                              20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
cttcatccgc tggaccgcca                                              20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
ctctcttcat ccgctggacc                                              20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285
gcctctcttc atccgctgga                                              20
```

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
ccacattgcc caggtctcca                                               20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
agccacattg cccaggtctc                                               20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288
gtcctttcca gcagccacat                                               20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
accgtccttt ccagcagcca                                               20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290
ggacacattg gccacaccgt                                               20

<210> SEQ ID NO 291
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 291
ttcaatggac acattggcca                                               20

<210> SEQ ID NO 292
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 292
tacggccaat gatggaatgc          20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293
gtggaccacc atagtacggc          20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294
gcttccagca tttccagtct          20

<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295
agccaagcgg cttccagcat          20

<210> SEQ ID NO 296
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 296
accacaagcc aagcggcttc          20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297
attgggcaat cccaatcaca          20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
gtttattggg caatcccaat          20

<210> SEQ ID NO 299

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
accacatagg gaatgtttat                                              20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
agaccacata gggaatgttt                                              20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301
actcagacca catagggaat                                              20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
tgagactcag accacatagg                                              20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
tgagtctgag actcagacca                                              20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
gatgagtctg agactcagac                                              20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
```

```
cagatgagtc tgagactcag                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
agcagatgag tctgagactc                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
ggacagcaga tgagtctgag                                               20

<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
tttagcagga cagcagatga                                               20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
agtttagcag gacagcagat                                               20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
tttctacagt ttagcaggac                                               20

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311
tttttctaca gtttagcagg                                               20

<210> SEQ ID NO 312
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 312
ttaagattac agtttaatgg                                              20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
tgttaagatt acagtttaat                                              20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314
tttccacctt tgcccaagtc                                              20

<210> SEQ ID NO 315
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 315
cttcagcacg cacacggc                                                18

<210> SEQ ID NO 316
<211> LENGTH: 650
<212> TYPE: DNA
<213> ORGANISM: R. norvegicus
<220> FEATURE:
<221> NAME/KEY: CDS
<222> LOCATION: (94)...(558)

<400> SEQUENCE: 316
gttttgcacc ttcgtttcct gcggcggctt ctgtcgtctc cttgcttttt gctctcccag    60
gttccgaggc cgccgcgcgt ctcccgggga agc atg gcg atg aag gcc gtg tgc   114
                                   Met Ala Met Lys Ala Val Cys
                                    1               5 gtg ctg aag ggc gac ggt ccg gtg cag ggc gtc att cac ttc gag cag    162
Val Leu Lys Gly Asp Gly Pro Val Gln Gly Val Ile His Phe Glu Gln
         10                  15                  20 aag gca agc ggt gaa cca gtt gtg gtg tca gga cag att aca gga tta    210
Lys Ala Ser Gly Glu Pro Val Val Val Ser Gly Gln Ile Thr Gly Leu
     25                  30                  35 act gaa ggc gag cat ggg ttc cat gtc cat caa tat ggg gac aat aca    258
Thr Glu Gly Glu His Gly Phe His Val His Gln Tyr Gly Asp Asn Thr
 40                  45                  50                  55 caa ggc tgt acc act gca gga cct cat ttt aat cct cac tct aag aaa    306
Gln Gly Cys Thr Thr Ala Gly Pro His Phe Asn Pro His Ser Lys Lys
                 60                  65                  70 cat ggc ggt cca gcg gat gaa gag agg cat gtt gga gac ctg ggc aat    354
His Gly Gly Pro Ala Asp Glu Glu Arg His Val Gly Asp Leu Gly Asn
```

|  |  |  |  |  |  |  |  |  |  |  |  |  |  |  |
|---|---|---|---|---|---|---|---|---|---|---|---|---|---|---|
|  |  | 75 |  |  |  | 80 |  |  |  | 85 |  |  |  |  |
| gtg | gct | gct | gga | aag | gac | ggt | gtg | gcc | aat | gtg | tcc | att | gaa | gat cgt |
| Val | Ala | Ala | Gly | Lys | Asp | Gly | Val | Ala | Asn | Val | Ser | Ile | Glu | Asp Arg |
|  |  | 90 |  |  |  | 95 |  |  |  | 100 |  |  |  |  |

402 gtg atc tca ctc tca gga gag cat tcc atc att ggc cgt act atg gtg    450
Val Ile Ser Leu Ser Gly Glu His Ser Ile Ile Gly Arg Thr Met Val
105             110             115 gtc cac gag aaa caa gat gac ttg ggc aaa ggt gga aat gaa gaa agt    498
Val His Glu Lys Gln Asp Asp Leu Gly Lys Gly Gly Asn Glu Glu Ser
120             125             130             135 aca aag act gga aat gct gga agc cgc ttg gct tgt ggt gtg att ggg    546
Thr Lys Thr Gly Asn Ala Gly Ser Arg Leu Ala Cys Gly Val Ile Gly
                140             145             150 att gcc caa taa acattccta tgtggtctga gtctcagact catctgctgt          598
Ile Ala Gln  * cctgctaaac tgtagaaaaa aaccaaacca ttaaactgta atcttaacag tt            650

<210> SEQ ID NO 317
<211> LENGTH: 7001
<212> TYPE: DNA
<213> ORGANISM: R. norvegicus

<400> SEQUENCE: 317
cagtaccagt aacaaaaaca ttagtgaaga ataagtaacg tggtatgtgc ccaggaatta     60
gaaacctgca gagagggtt ggggatttag ctcagtggta gagcgcttgc ctaggaagcg    120
caaggccctg ggttcgattc cccagctccg aaaaaaagaa cccccccca aaaaaaaga     180 aacctgcaga gaaaaaaaaa aaacctgcag agacacagag gtgtgtctgg agatagaaca    240
tgggccttac acatattaca ccgagcatcc atcttggctc accccaactt tcacacagca    300
actgcggcgc gctgcaaagt cagtcgcaat ccgcatttct agacagagcg gcttcagacc    360
ttccaggcgc gcacgcaggc ctcgccgagg ttctcggttt ccgccgcgac tcggccgacg    420
tcacagttag aagacaatag cgactttccc agctctgtct cgattctgga actttctcag    480
tccgcaagct cctgaagctg gcgctcccct cagccccgcc ccaacgtgc cccgcggcca     540 gggaacttca ggaagggtag gcagagaccg cggctagcga ttggttccct gccaaggtgg    600
gagtggccag gcgcaggcat ataaaagctc gcggcgctg ggcccctcgtt ttgcaccttc     660 gtttcctgcg gcggcttctg tcgtctcctt gcttttgct ctcccaggtt ccgaggccgc    720
cgcgcgtctc ccggggaagc atggcgatga aggccgtgtg cgtgctgaag ggcgacggtc    780
cggtgcaggg cgtcattcac ttcgagcaga aggcaaggcc cggggcgctg gcgcaggcc     840 gcggtgacgc ggggcacctg tgcgggagca gccacgcccc cgccgcggc ctgagcccgt     900 taaatgctga gtcaccgcgg ccttgaggca ggggccgggc gcgggagagg gaggccgggg    960
cgccgcgggg ccttccgggc gggtccctct tcgcgccccc gagtggccgg gccggccga   1020 gagagcgggc ttggcatccg ctatccctct ggggctgctg cttttccggt gtccctgtcc   1080
cacaggggct cagaccccttg tggccaccgg ctgcatttgt tgtaagaata tttgaacctg   1140
gtggtgccaa accggactaa cgcagcaagc agaacgcatt tgtggcattt taaagccaag   1200
ccctggctat attaggtcag ggtcgtgccg caagggggaa agaaaagaga tggccttggg   1260
cagttgtttt gccaccaaga gctccaagaa agagacctga ctctggttgt tgtctacgac   1320
agcgagtctc tgagcacaat ttgaaaagta tacagaaata tttttcgaaac tactgcagtt   1380 ctgcaaaaac acatgcgtca caaggaagat atttgtgtgg ttaagagcgt gttcagagcc   1440

```
ttagggggtt aacattgtac tccttttaat cccgagagaa atatttgata aatgagcgtt   1500
atgtactctc taaagtggtt tacataaatg tgaggagacc gacaccatag tgaatccaag   1560
tgtttccttt atgaggagaa ctgataacgg gaatttagag tttttcataa ctagtctcag   1620
tttcttggca tttaaatgta ttttgttgtt ttcctgtgta aattttttgt ttttgtcttt   1680
ctcttcttcc cacataattc actgtgagac agggcttttc ccccaccctg agaaagctga   1740
agactagcta ggtctacccc agtgtccacc ttcccagagc agcttgcagc attctttggt   1800
gacgctgccc tttgtacccg atcaaacgat agttaagcat tccaggttgg cagctgtaac   1860
aacttgacta tcaaaactgt ttgatttaaa ctgttgccaa cttttcaaaa tcagtttttt   1920
tctactcaaa gttcctagtc ccttattttg ttgaaaacgt tggagagtta aagtagaaag   1980
gtccggtatg agtgtccttg tttgttgcag ttggttgcgt cttgcctttt ctccctgttg   2040
ctacaatttc tgaagtaata ctaaatttga attttggatg ttcttttctt ttttgttaag   2100
tagcaaattc tctagatttg gatgcctaat gagactttt taaaaagtag ctctggttag   2160
acccaaatgg atccccacag gcagtaggac acaattattt tctggctact ggataaaatt   2220
atgggaactg ataaacatca ctgaatgtgg agtagaggtt tctgggcagc caatgttctg   2280
aaagaatcaa gcctgacaca gtgcagtagc catccattcc ctagttctga cattgagctg   2340 ccccctttg ttcctctggg tgcttttcaa gtgctgttga gtccaggtgt ctgcacacgt   2400
gcatctggaa acaagtgtta gggaagatgg gtagggaggg agaggcctag agctaagcag   2460
ctctagagtc accctggagg aaatgggtct acttggattt ggacataggt ttgattttgt   2520 tttgttttt gacttgtgcc ttttactgtg attcagaagt attaacacaa acttgatgtc   2580 ttaattttg tattttttta aataaaggca agcggtgaac cagttgtggt gtcaggacag   2640
attacaggat taactgaagg cgagcatggg ttccatgtcc atcaatatgg ggacaataca   2700
caaggtaagt cttaatctat ctctacctgg ctgactagtg agatgaatgg gactgagtca   2760
ggaccaatta ctaaccattt aaaaccatca attttttct ttttcttta gattaagtta   2820 aaataaccac ttaggtcaac ctcggaaaat agccacaaaa gtattttagt tagtatcgag   2880
tatttcttga ctccttaagt gggaaggtga gggtaaattt tcttaaatgt gattattata   2940
gcttgacttt aatatacaga aacaaatacg caccttcctt attttggata atcctttgag   3000
gtgtttggag ctgggggttg agggtgggtg cttaggcac agtgtctaag gacagctatg   3060
cacgagaggc atagtgggac agaagtgaca aaaactgaag attcaatata aatgcttaga   3120
gtaaaatttt ttatatttgg gattggaatc aagtcagaaa atatagtggc ttacattgca   3180
tttagtgaac ttttaccata ttggagtaat gatctgtgtt tgtttataat cttttaagag   3240
cctcattcat gttgctagag cctttctctc ctttccctct tctccctgc tttccctcc   3300 ccacatagtg catgctagcc tggaatctgt gctggagctt aaaccattta gtcttagatg   3360
tgcagggtta aaggccatca acctgtgtgc aatgtacagt aatttggcct acagttactt   3420
atgtttgtgt ttgacccatt cggataatta ctaaagttca atcaagttgc tttgcctctg   3480
gcctggtagc tttggtttgt taagttcctt ccagaatcct gccctgtacc tatttcttgg   3540
tctgggtaga aattgtaaac tatgtaagtc ctatttcctg agttgttgtt gctgttgaga   3600
tgtcccttgt gaatgatgtc ccttagccca catgtacacc tctaatgctg tttacacctg   3660
gagttgagaa gcacagcagc cttgacacgt ggggataatc taaaaatctg tctgccccaa   3720
gtaaaagcca gatggctgag ctgttggtg gtgtaaggtc ttgaaagata agtgttttta   3780
tcatgatctt aaaagcaaag atctttaaat gtgggacttt aactttagaa gtgccactaa   3840
```

```
aggtcgcttc tgttccagta gaggaaggaa ccagagctag acatgctgtg acactaccat   3900
gctcctggca cttggaaggc taaggtagga gggtcattaa ctgcagatat catgggctgt   3960
ggtagtgaga ccctgtctca aatctcaaaa caaacaaaca tgacagtcta gtgaaaaagc   4020
gggtagcttg aaaatgcaag gccatatagt ccagctattt gtaccagggt gctgcttcct   4080
gtttgtatca ctccagcaca taccagctcc atgtttgctg tgttggaagt tgtaagaatt   4140
ccgatgtcat tgcatacaga ggtttacttc ataatctgac tgctggtttc tggtaaatag   4200
gctgtaccac tgcaggacct cattttaatc ctcactctaa gaaacatggc ggtccagcgg   4260
atgaagagag gtgagcagca ttctctctat gcatggtggt ggagaggggt ctgtggaaaa   4320
cacctgaaga cagaactgag tggtctcact gccttttctt ttgtatgttt ccattcaccc   4380
aactcccaca tccccaagta ctggaatagt ttatattggg tgaaggagct gacaaatgtg   4440
gactcttaag tgatttagtt ttgtagcatt tattgaagat gaactaatac aagtgccaaa   4500
aggaaccaat acagaaaata tcatggataa cagtactatc agtcactagc aaagtaaatc   4560
attgtataat atactaatgc agataataaa aactagttga gattccgttt gtatgtgaaa   4620
ccttaggaaa gtcctacatt taaagagggg ctagcttgct tttggaatgg aggcctggga   4680
gcaaaccttt gctaatcagg agctgacatc cttttcgaaa gtcctagact gtggctctct   4740
cctttaaact ggaagagcta tgtgtcaagg tatcctggct acctgttttg aaatttgtgt   4800
ttccagacct ttgtctggaa aagccatcat atttgatagt gtatgtgcac tctttaatcc   4860
actcatagca tttgacttcg atgtgaattt agctattgaa ctctattgat gtgaaataga   4920
tatcattgct tatccacctg gtgctgtttt aatgttaggc atgttggaga cctgggcaat   4980
gtggctgctg gaaaggacgg tgtggccaat gtgtccattg aagatcgtgt gatctcactc   5040
tcaggagagc attccatcat tggccgtact atggtggtaa gtttccatat agtagtagat   5100
gtaggatttc ttctaacata gttatgtacc ttttccatgac ttcgtggtgg tggttaaact   5160
agttcctaaa agatcacata aattggtaag agttcagaat aggaaaaaat attattttat   5220
tggatgtaat agtaaagaat taatttgcct aggtcagtta agaacgctgt tctgctgaag   5280
tgcggtagaa agctggttac atttgatcag actggatctg agttgaggat acaatagtct   5340
ttagtttaaa acagctggat tttcttgcca tgattgcccc cttacagtta atcatttcgt   5400
tgagcttaaa atctgcgatg gatgtcagta ttcaagtctg caggttatcg cttggttacc   5460
atatgggagc cgtcttccca gttaccctc gggagatgaa tctggttcat gcagaacacc   5520
aagtagtaaa agctcttgcc cacttcgggc agctaacttt tcagtaggca cttcctttca   5580 gttgacccctt tatccttaga attttcttca gccctattgg tgaagcagaa caatcattca   5640
taaatgttct aaaaataaaa tttaaaatct tgttgctaag taaagatatt tagaattgcc   5700
tcttatgtgt aggcctatag ttcactcacc aagagatttt gatagagaaa tttgtaagaa   5760
tgactactgt acagtggggt gagggtgagg gctaagatca gcatgtgcct ggtagttatt   5820
tgggtcctta gtattcatct agaaatagcc acgagcaagg aaacacttag tagtctgctt   5880
ttagctgata gcataaaaat tagcttattg atttactaat agatttgaac attttctaat   5940
atacatggtc ctttgaagta ttgctgggaa gaagtgctaa ttacttgatc accgaaacct   6000
aaatgttctt aattcttttc aaaggtccac gagaaacaag atgacttggg caaaggtgga   6060
aatgaagaaa gtacaaagac tggaaatgct ggaagccgct tggcttgtgg tgtgattggg   6120
attgcccaat aaacattccc tatgtggtct gagtctcaga ctcatctgct gtcctgctaa   6180
```

```
actgtagaaa aaaaccaaac cattaaactg taatcttaac agttgttaac tgtgtgactc    6240
ctttgacttg ctctaaggac ttgcagtgag aggtgactga cgatgtttgg aggatgtgta    6300
gaacttcctg aatgtgtaca actcattgaa ctaaaatctg ttgtttctgt gccagacctc    6360
actggtgtta agctgaaatt ctcattcaag cctctctctc tctctgtgtg tgtctgtgtg    6420
tgtgtgtgtg tgtgtgtgtg tgtgtgtgtg tgtgtgtgtg tgtgtgtgtg tgtgtgagag    6480
agactgagac ttatttagag cctcgagaga tagagactta tttcaagcct attaatgtat    6540
accaaaaaga cctaagctct atacactgag catcaacaac agactcaatg aggctctcat    6600
agtatttaat tttgaaagtg tttcatgtga taccatcaaa atgacgtgtg gtagcccaaa    6660
ccggatttga tcttagaaaa ttttctgccc tttgttatca tcagaaatta ctgaaagctc    6720
tctttaagat tcagagtacc taaccttatt ttaaaatcgt attagagtta gaagccatga    6780
tttaagataa agccctttag taaacttgta taaaactcat aaaaggcaaa taggtagcct    6840
cagctagcca agtttaatac ctcctctacc tgccaagtga agttggtacc acctgctttt    6900
ttaaggttgg cactcaggaa atacatagca ctgggagatg agaccaagtg gttctggcgg    6960
ttgtggctaa atcgactttt acagcctcag ttaatgaaac t                       7001

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
caccgcttgc cttctgctcg                                                 20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
tctcgtggac caccatagta                                                 20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
tgcaaaacga gggcccagcg                                                 20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321
gggccttgcc ttctgctcga                                                 20

<210> SEQ ID NO 322
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 322
caccgcttgc ctttatttaa                                              20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
ttaagactta ccttgtgtat                                              20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
gtggtacagc ctatttacca                                              20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
tgctgctcac ctctcttcat                                              20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
tccaacatgc ctaacattaa                                              20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
ggaaacttac caccatagta                                              20

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
```

-continued

```
tctcgtggac ctttgaaaag                                              20

<210> SEQ ID NO 329
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 329
cgcttgcctt ctgct                                                   15

<210> SEQ ID NO 330
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 330
cgtggaccac catag                                                   15

<210> SEQ ID NO 331
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 331
aaaacgaggg cccag                                                   15

<210> SEQ ID NO 332
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 332
ccttgccttc tgctc                                                   15

<210> SEQ ID NO 333
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 333
cgcttgcctt tattt                                                   15

<210> SEQ ID NO 334
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 334
agacttacct tgtgt                                                   15

<210> SEQ ID NO 335
<211> LENGTH: 15
<212> TYPE: DNA
<213> ORGANISM: Artificial Sequence
```

```
<220> FEATURE:
<223> OTHER INFORMATION: Antisense Oligonucleotide

<400> SEQUENCE: 335
gtacagccta tttac                                                    15

<210> SEQ ID NO 336
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 336
tgctcacctc tcttc                                                    15

<210> SEQ ID NO 337
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 337
aacatgccta acatt                                                    15

<210> SEQ ID NO 338
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 338
aacttaccac catag                                                    15

<210> SEQ ID NO 339
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 339
cgtggacctt tgaaa                                                    15

<210> SEQ ID NO 340
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 340
cgagaggcgg acgggaccgt t                                             21

<210> SEQ ID NO 341
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 341
cggtcccgtc cgcctctcgt t                                             21
```

```
<210> SEQ ID NO 342
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 342
cgagaggcgg acgggaccg                                                19
```